United States Patent
Yamagata

(10) Patent No.: US 9,155,518 B2
(45) Date of Patent: Oct. 13, 2015

(54) ULTRASOUND IMAGING APPARATUS AND METHOD FOR GENERATING ULTRASOUND IMAGE

(75) Inventor: Hitoshi Yamagata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 513 days.

(21) Appl. No.: 12/464,516

(22) Filed: May 12, 2009

(65) Prior Publication Data

US 2009/0306511 A1 Dec. 10, 2009

(30) Foreign Application Priority Data

Jun. 9, 2008 (JP) ................................ 2008-150569

(51) Int. Cl.
*A61B 8/00* (2006.01)
*A61B 8/08* (2006.01)
(Continued)

(52) U.S. Cl.
CPC ............. *A61B 8/0833* (2013.01); *A61B 8/0841* (2013.01); *A61B 8/14* (2013.01); *A61B 8/483* (2013.01); *A61B 8/523* (2013.01); *G01S 7/52085* (2013.01); *G01S 15/899* (2013.01); *G01S 15/8925* (2013.01); *G01S 15/8993* (2013.01);
(Continued)

(58) Field of Classification Search
CPC ............. A61B 8/00; A61B 8/14; A61B 8/52; A61B 5/0048; G01S 15/8993; G01S 15/8995
USPC ......... 600/407, 423, 424, 437, 441, 442, 443, 600/445, 446, 447, 456, 463, 464; 73/584, 73/586, 587, 589, 620, 627, 861, 861.06, 73/861.23

See application file for complete search history.

(56) References Cited

U.S. PATENT DOCUMENTS

| 5,967,985 A | 10/1999 | Hayakawa |
| 6,081,577 A * | 6/2000 | Webber ........................... 378/23 |
| 6,245,017 B1 * | 6/2001 | Hashimoto et al. ........... 600/447 |
| 6,336,899 B1 * | 1/2002 | Yamazaki ...................... 600/443 |

(Continued)

FOREIGN PATENT DOCUMENTS

| CN | 101176675 A | 5/2008 |
| JP | 2007-125169 | 5/2007 |
| JP | 2007-215672 | 8/2007 |

OTHER PUBLICATIONS

Chinese Office Action mailed Aug. 13, 2010 in corresponding Chinese Application No. 200910137898.

*Primary Examiner* — Unsu Jung
*Assistant Examiner* — Michael N Fisher
(74) *Attorney, Agent, or Firm* — Oblon, McClelland, Maier & Neustadt, L.L.P.

(57) ABSTRACT

For a three-dimensional region including a treatment target site of a patient, a puncture needle scanning region R1 having a slice thickness d1 is set with reference to a cross section (a puncture cross section) including an insertion direction of a puncture needle. Subsequently, in the y-direction substantially perpendicular to the puncture cross section, two treatment target scanning regions R2 (R21 and R22) each being adjacent to the puncture needle scanning region R1 and having a slice thickness d2 are set. Then, based on volume data in the puncture needle scanning region R1 acquired by first three-dimensional scan with ultrasound waves and volume data in the treatment target scanning regions R2 acquired by second three-dimensional scan performed at a lower volume rate than the first three-dimensional scan, image data is generated for the purpose of supporting puncture.

21 Claims, 14 Drawing Sheets

(51) Int. Cl.
*A61B 8/14* (2006.01)
*G01S 15/89* (2006.01)
*A61B 8/06* (2006.01)
*A61B 8/13* (2006.01)
*G01S 7/52* (2006.01)

(52) U.S. Cl.
CPC .... *A61B 8/06* (2013.01); *A61B 8/13* (2013.01); *G01S 7/52063* (2013.01); *G01S 7/52074* (2013.01)

(56) References Cited

U.S. PATENT DOCUMENTS

| | | | |
|---|---|---|---|
| 6,341,152 B1 * | 1/2002 | Sugihara | 378/4 |
| 2004/0102704 A1 | 5/2004 | Tsujita et al. | |
| 2005/0203414 A1 * | 9/2005 | Greppi et al. | 600/461 |
| 2006/0100515 A1 * | 5/2006 | Nakata | 600/441 |
| 2007/0167769 A1 * | 7/2007 | Ikuma et al. | 600/437 |
| 2008/0114243 A1 | 5/2008 | Oonuki | |
| 2008/0242971 A1 * | 10/2008 | Klingenbeck-Regn | 600/407 |
| 2008/0262348 A1 * | 10/2008 | Hashimoto et al. | 600/437 |

* cited by examiner

R1 : PUNCTURE NEEDLE SCANNING REGION
R2 : TREATMENT TARGET SCANNING REGION
Sb : PUNCTURE CROSS SECTION

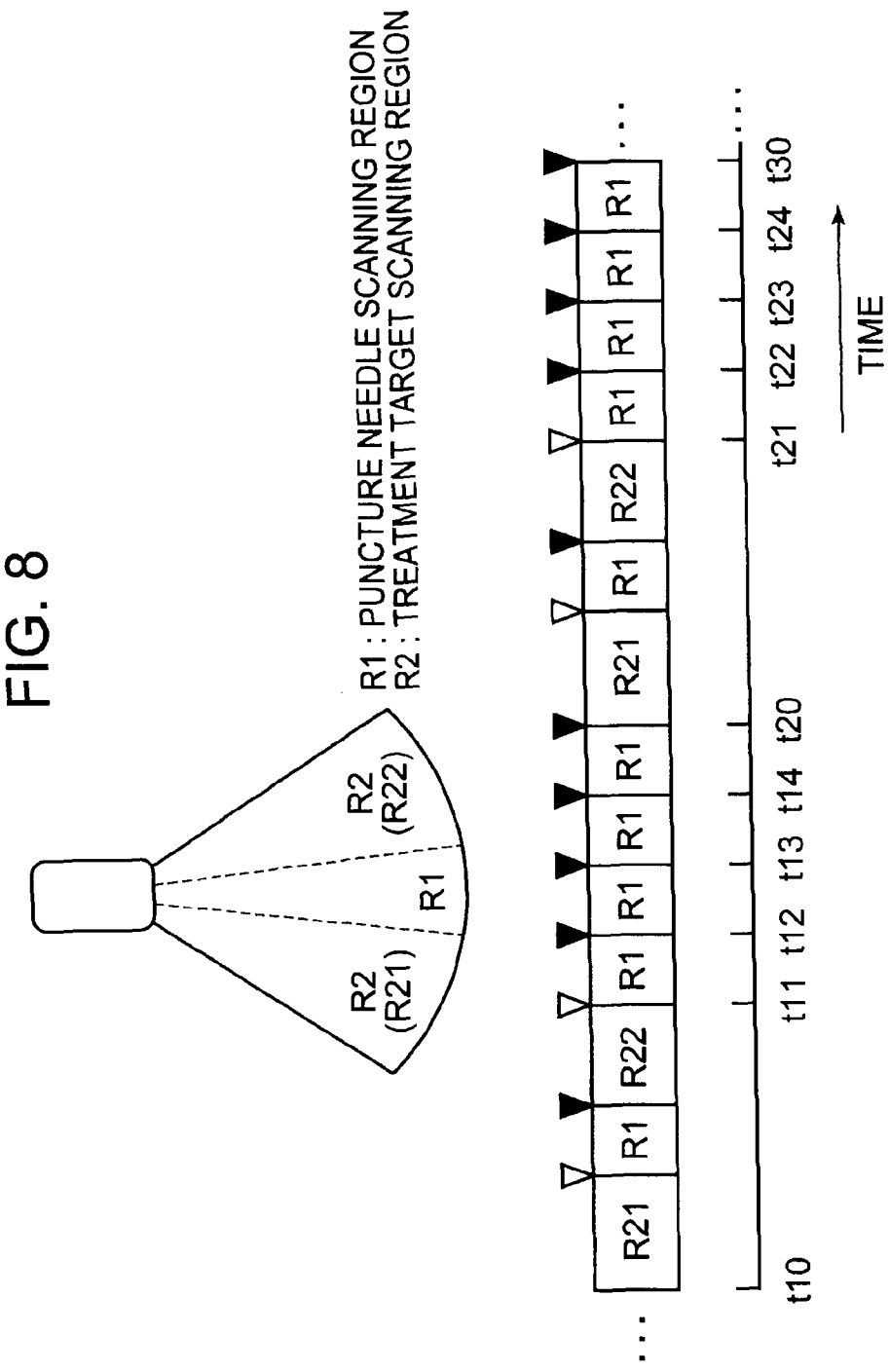

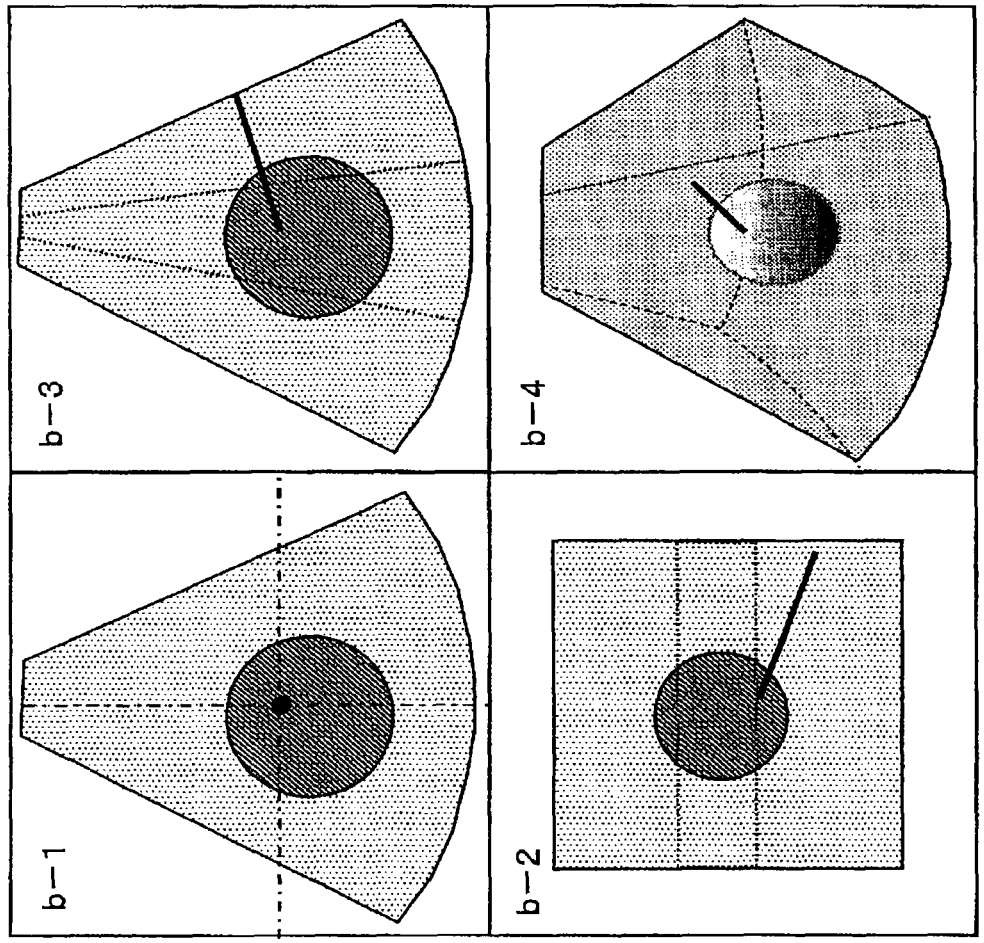
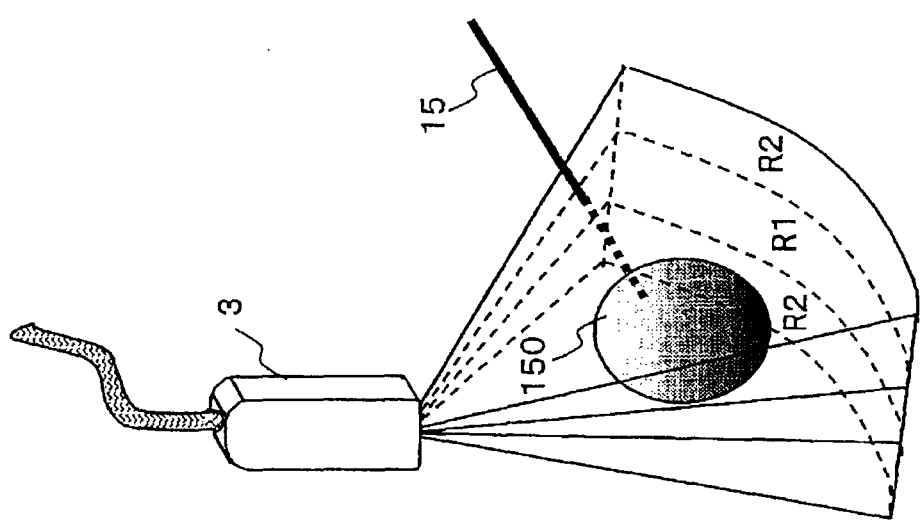

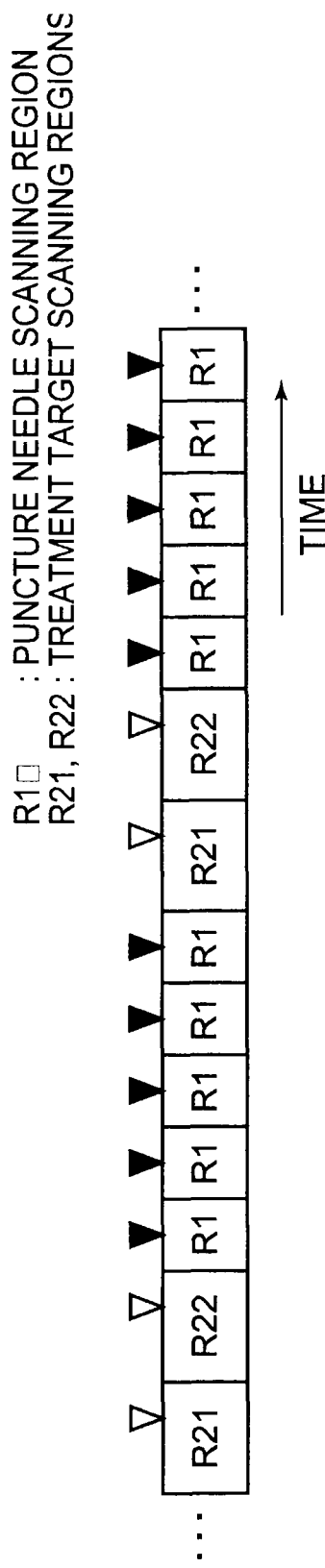
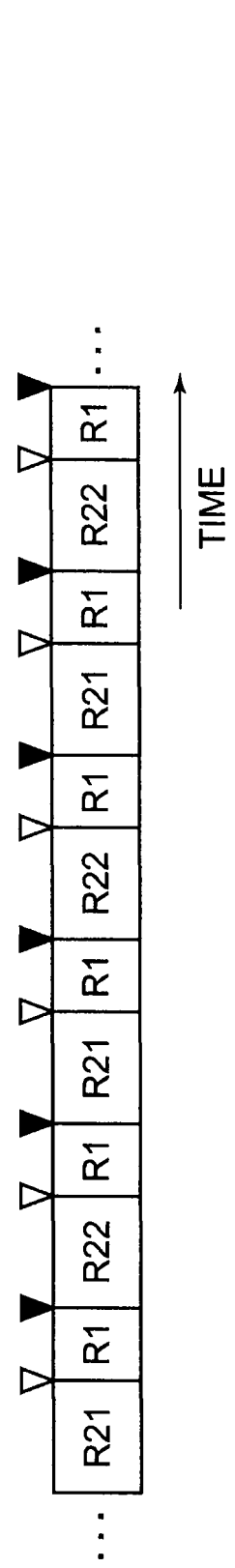
FIG. 11A
FIG. 11B
R1 □ : PUNCTURE NEEDLE SCANNING REGION
R21, R22 : TREATMENT TARGET SCANNING REGIONS
▶ : TIMING OF GENERATION/UPDATE OF VOLUME DATA IN PUNCTURE NEEDLE SCANNING REGION
▽ : TIMING OF GENERATION/UPDATE OF VOLUME DATA IN TREATMENT TARGET SCANNING REGION

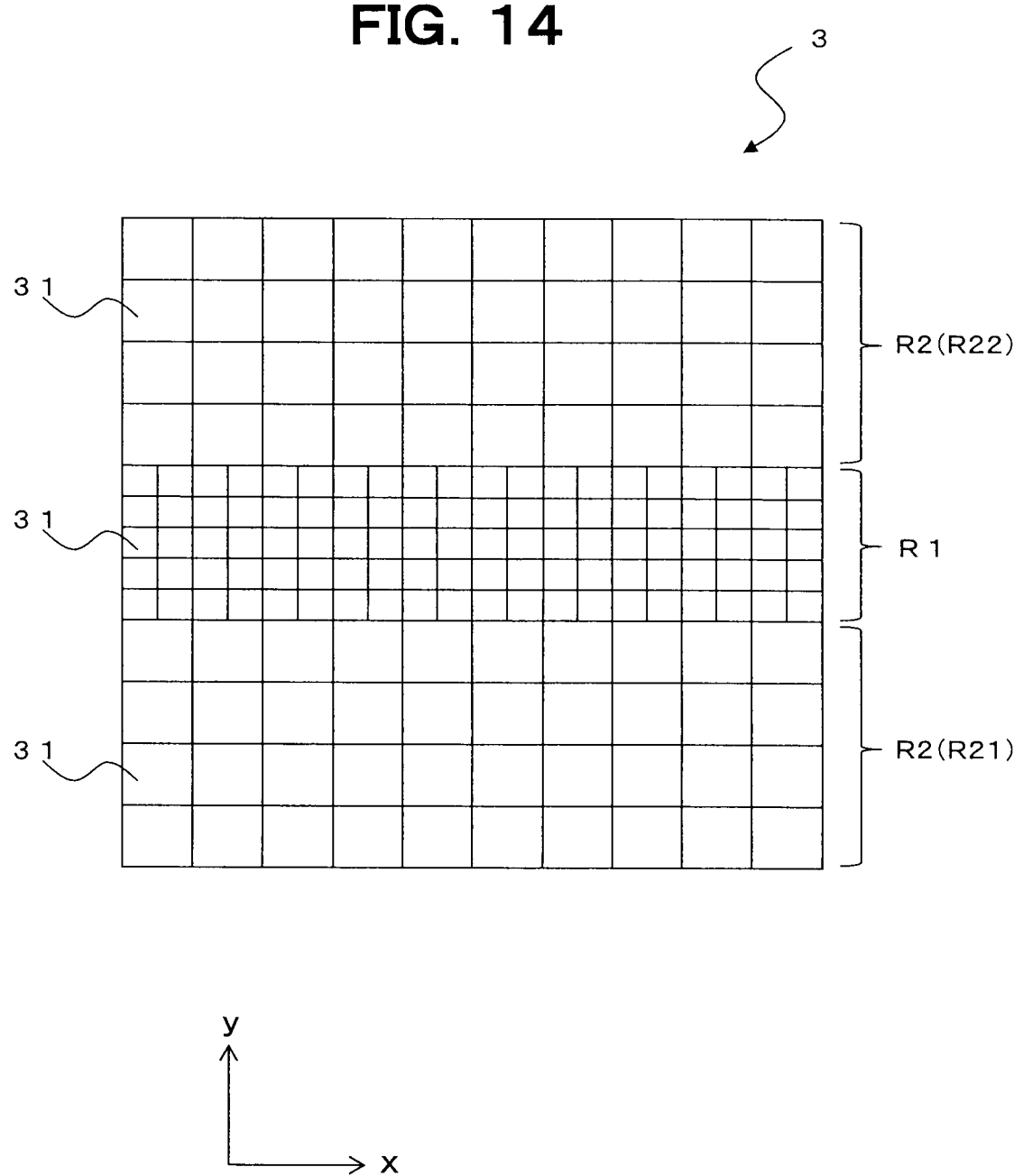

ULTRASOUND IMAGING APPARATUS AND METHOD FOR GENERATING ULTRASOUND IMAGE

BACKGROUND OF THE INVENTION

1. Field of the Invention

The present invention relates to an ultrasound imaging apparatus that generates image data for supporting treatment and examination using a puncture needle, and also relates to a method for generating an ultrasound image.

2. Description of the Related Art

The mortality rate for cancer, which is one of the three major diseases, has been increasing yearly, and early diagnosis and treatment of cancer is strongly desired. For example, liver cancer accounts for approximately 10% of all cancers, and the percentage has been increasing. On the other hand, advancement of the technology of medical image diagnosis apparatuses such as an ultrasound imaging apparatus, an MRI apparatus and an X-ray CT system is remarkable, and medical image diagnosis apparatuses has been essential for early detection of various cancers including liver cancer mentioned above.

To be specific, three-dimensional imaging by an X-ray CT system, which is combination of high-speed rotation helical scan with a multi-detector of, e.g., 64 rows, has been in practical use. Moreover, owing to increase in performance of gradient magnetic field systems, high-frequency magnetic field systems and RF coil systems, three-dimensional imaging by an MRI apparatus capable of high-speed imaging has been in practical use.

Observation of volume rendering image data, etc., obtained by these three-dimensional imaging methods has significantly increased the diagnostic ability as compared with a conventional two-dimensional imaging method.

On the other hand, an ultrasound imaging apparatus allows real-time observation using two-dimensional image data by a simple operation of making an ultrasound probe in contact with a body surface. Besides, a method of acquiring three-dimensional B-mode image data and color Doppler image data in real time by using an ultrasound probe in which transducers are one-dimensionally arranged and mechanically oscillating the transducers has been developed. Moreover, another method of acquiring three-dimensional B-mode image data and color Doppler image data in real time by using a so-called 2D array probe in which transducers are two-dimensionally arranged has been developed.

As a method for treating liver cancer mentioned above, (a) anticancer agent injection into the liver artery, (b) transcatheter arterial embolization (TAE), (c) minimally invasive therapy, (d) laparotomy, etc., are common. In recent years, the minimally invasive therapy with a simple procedure and less burden on a patient is particularly remarkable. The minimally invasive therapy includes the PEIT (Percutaneous Ethanol Injection Technique) and microwave ablation. A puncture needle used in these therapies is inserted into a patient with observation of an image displayed in real time.

Further, in recent years, RFA (Radio Frequency Ablation) has been attracting attention as one of the ablation therapies, and clinical application thereof has already begun. In this RFA, Cool Tip, which is a single needle, or RITA, which is an expandable needle, is used as the puncture needle. The puncture needle is usually inserted into a tumor percutaneously from the body surface with observation of an image, but may be inserted with observation of the surface of the liver by a laparoscope. Moreover, the puncture needle may be inserted with observation of an ultrasound image acquired by a special small ultrasound probe placed on the surface of the liver.

By performing the abovementioned puncture therapy with observation of two-dimensional image data acquired in real time by an ultrasound imaging apparatus, the efficiency of the therapy and the safety of the therapy have been drastically increased. Besides, in recent years, various puncture therapies performed with observation of a three-dimensional image have been proposed (e.g., Japanese Unexamined Patent Application Publication No. 2007-125169 and Japanese Unexamined Patent Application Publication No. 2007-215672).

With the method according to the conventional art of performing the puncture therapy with observation of three-dimensional image data acquired in real time by an ultrasound imaging apparatus, it is possible to three-dimensionally grasp the insertion direction of a puncture needle, the position of the tip, or the like. Therefore, it is possible to further increase the accuracy of insertion of a puncture needle into a treatment target site as compared with the puncture therapy performed with observation of two-dimensional image data.

However, it is difficult to acquire three-dimensional image data representing a wide range that satisfies both high spatial resolution and high temporal resolution (real-time property). Therefore, with the method according to the conventional art described above, in the case of acquiring image data representing a relatively wide treatment target site including liver cancer or the like, and image data representing a puncture needle inserted into this treatment target site and an area surrounding the puncture needle, it is difficult to simultaneously acquire image data representing a treatment target site that requires high spatial resolution and image data representing a puncture needle and an area around the puncture needle that requires high temporal resolution and high spatial resolution in order to track the tip of the puncture needle.

SUMMARY OF THE INVENTION

An object of the present invention is to provide an ultrasound imaging apparatus that, when a puncture needle is inserted into a patient with observation of image data acquired by three-dimensional scan with ultrasound waves on the patient, can almost simultaneously acquire image data representing a treatment target organ and image data representing the puncture needle and an area surrounding the puncture needle with higher temporal resolution than the former image data, and also provide a method for generating an ultrasound image.

A first aspect of the present invention is an ultrasound imaging apparatus that generates image data based on volume data acquired by three-dimensional scan with ultrasound waves on a target site for examination or treatment using a puncture needle, comprising: a scan controller configured to set a first three-dimensional scanning region including an insertion direction of the puncture needle into the target site and one or more second three-dimensional scanning regions adjacent to the first three-dimensional scanning region, and control three-dimensional scan on the first three-dimensional scanning region and the second three-dimensional scanning regions; a volume data generator configured to generate volume data based on received signals acquired from the first three-dimensional scanning region and the second three-dimensional scanning regions by the three-dimensional scan; an image data generator configured to generate image data by processing the volume data; and a display configured to display the image data, wherein: the scan controller executes control for three-dimensionally scanning the first three-dimensional scanning region at a higher volume rate than the second three-dimensional scanning regions.

According to this first aspect, when a puncture needle is inserted into the patient with observation of image data acquired by three-dimensional scan with ultrasound waves, it is possible to almost simultaneously acquire image data representing a treatment target organ and image data representing the puncture needle and an area surrounding the puncture needle with higher temporal resolution than the former image data. Thus, accurate insertion of the puncture needle in a desired position of an examination target organ or a treatment target organ is facilitated. This increases safety and efficiency in examination or treatment using a puncture needle and makes it possible to reduce the burden on the operator and the patient.

Further, a second aspect of the present invention is an ultrasound imaging apparatus that generates image data based on volume data acquired by three-dimensional scan with ultrasound waves on a target site for examination or treatment using a puncture needle, comprising: a scan controller configured to set a first three-dimensional scanning region including an insertion direction of the puncture needle into the target site and one or more second three-dimensional scanning regions adjacent to the first three-dimensional scanning region, and control three-dimensional scan on the first three-dimensional scanning region and the second three-dimensional scanning regions; a volume data generator configured to generate volume data based on received signals acquired from the first three-dimensional scanning region and the second three-dimensional scanning regions by the three-dimensional scan; an image data generator configured to generate image data by processing the volume data; and a display configured to display the image data, wherein: the scan controller executes control for scanning the first three-dimensional scanning region at a higher scanning-line density than the second three-dimensional scanning regions.

Moreover, a third aspect of the present invention is a method for generating an ultrasound image in which image data is generated based on volume data acquired by three-dimensional scan with ultrasound waves on a target site for examination or treatment using a puncture needle, comprising: setting a first three-dimensional scanning region including an insertion direction of the puncture needle into the target site and one or more second three-dimensional scanning regions adjacent to the first three-dimensional scanning region, controlling three-dimensional scan on the first three-dimensional scanning region and the second three-dimensional scanning regions, and executing control for three-dimensionally scanning the first three-dimensional scanning region at a higher volume rate than the second three-dimensional scanning regions; generating volume data based on received signals acquired from the first three-dimensional scanning region and the second three-dimensional scanning regions by the three-dimensional scan; generating image data by processing the volume data; and displaying the image data.

Moreover, a fourth aspect of the present invention is a method for generating an ultrasound image in which image data is generated based on volume data acquired by three-dimensional scan with ultrasound waves on a target site for examination or treatment using a puncture needle, comprising: setting a first three-dimensional scanning region including an insertion direction of the puncture needle into the target site and one or more second three-dimensional scanning regions adjacent to the first three-dimensional scanning region, controlling three-dimensional scans on the first three-dimensional scanning region and the second three-dimensional scanning regions, and executing control for scanning the first three-dimensional scanning region at a higher scanning-line density than the second three-dimensional scanning regions; generating volume data based on received signals acquired from the first three-dimensional scanning region and the second three-dimensional scanning regions by the three-dimensional scan; generating image data by processing the volume data; and displaying the image data.

BRIEF DESCRIPTION OF THE DRAWINGS

FIG. 8 is a time chart illustrating the order of three-dimensional scans on a puncture needle scanning region and treatment target scanning regions and the timing of update of volume data according to this embodiment.

FIG. 10A is a view illustrating a modification of treatment target scanning regions and a puncture needle scanning region set in this embodiment.

FIG. 10B is a view illustrating a specific example of display data generated by the display data generator according to this embodiment.

FIG. 11A is a view illustrating a modification of the order of three-dimensional scans on a puncture needle scanning region and treatment target scanning regions according to this embodiment.

FIG. 11B is a view illustrating a modification of the order of three-dimensional scans on a puncture needle scanning region and treatment target scanning regions according to this embodiment.

FIG. 14 is a view illustrating the arrangement of transducers in an ultrasound probe compatible with convex scan or linear scan of the ultrasound imaging apparatus according to the embodiment.

DETAILED DESCRIPTION OF THE EMBODIMENTS

An ultrasound imaging apparatus according to an embodiment of the present invention will be described below with reference to the drawings.

In the embodiment of the present invention described below, for a three-dimensional region including a treatment target site of a patient, a puncture needle scanning region having a predetermined slice thickness is firstly set with reference to a cross section (may be referred to as a "puncture cross section" hereinafter) including an insertion direction of a puncture needle inserted along a needle guide of a puncture adapter attached to an ultrasound probe. Subsequently, in the y-direction (normal direction) substantially perpendicular to the puncture cross section, a treatment target scanning region having a predetermined slice thickness adjacent to the puncture needle scanning region is set. Then, based on volume data in the puncture needle scanning region acquired by first three-dimensional scan with ultrasound waves and volume data representing the treatment target scanning region acquired by second three-dimensional scan executed at a lower volume rate than in the first three-dimensional scan, image data for the purpose of supporting puncture is generated.

Although an ultrasound imaging apparatus that supports treatment using a puncture needle (puncture treatment) will be described below, an ultrasound imaging apparatus may be configured to support examination using a puncture needle.

(Configuration of Apparatus)

Figure 1:
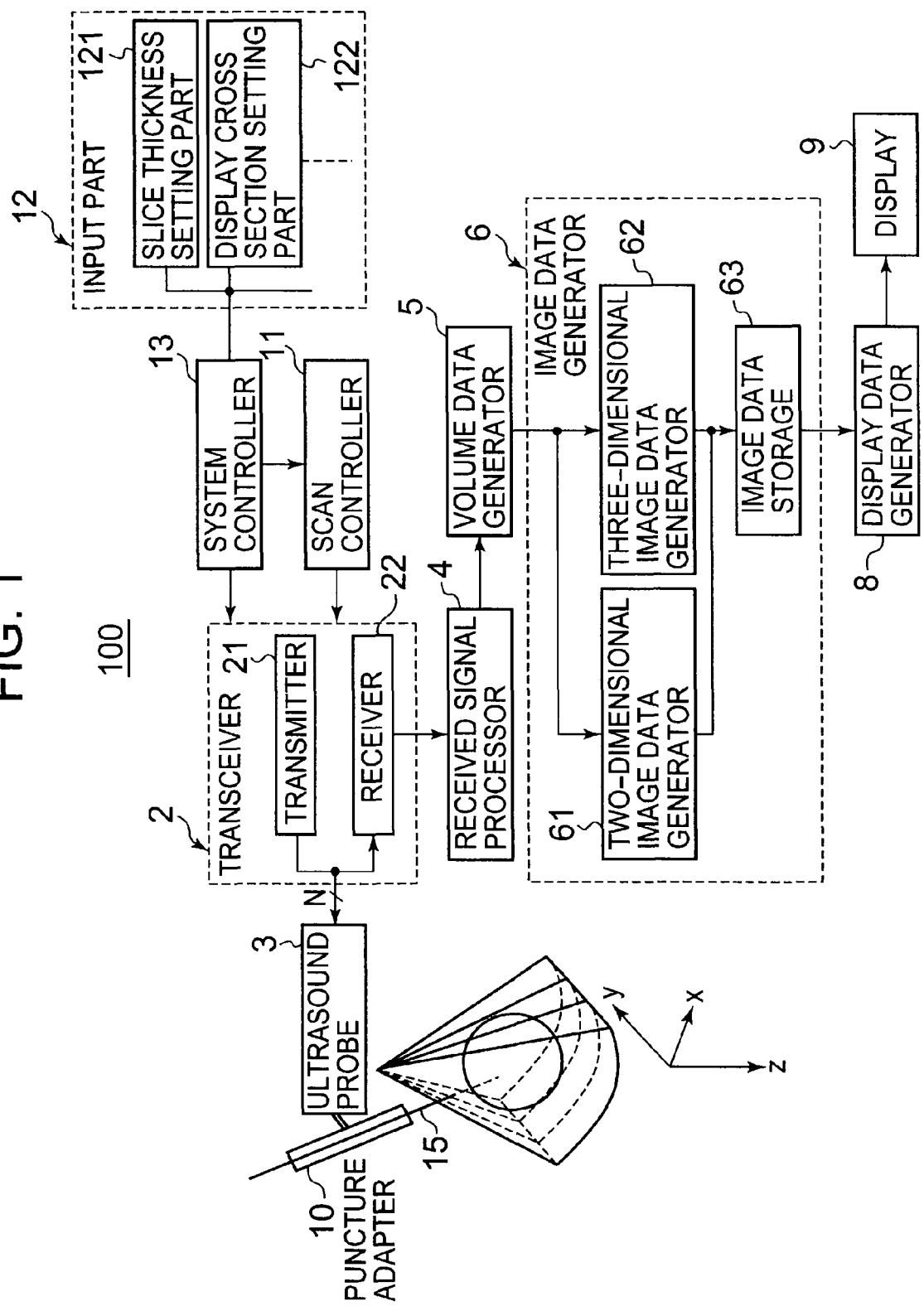
FIG. 1 is a block diagram illustrating an ultrasound imaging apparatus according to an embodiment of the present invention.
Figure 2:
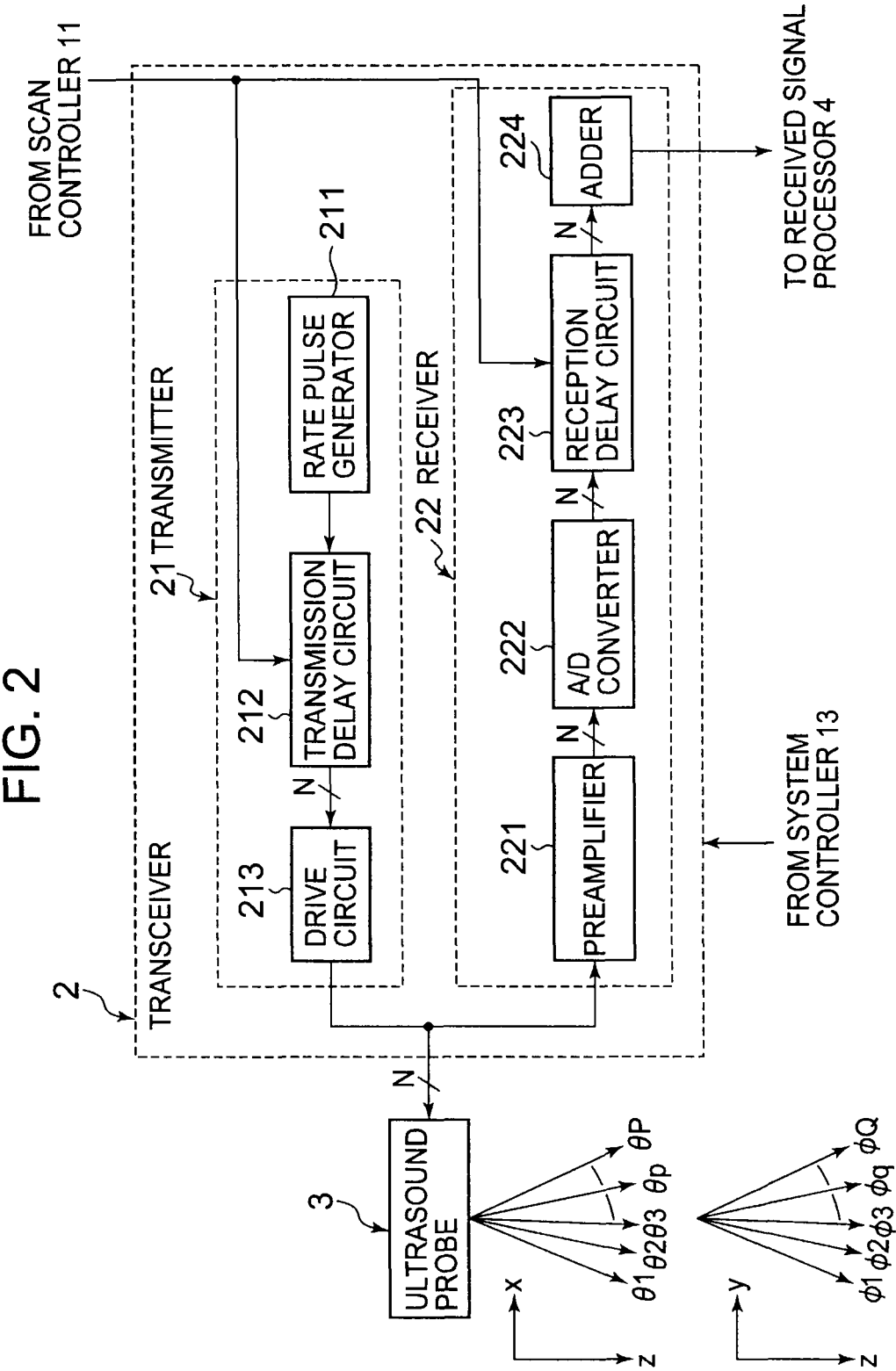
FIG. 2 is a block diagram illustrating a transceiver of the ultrasound imaging apparatus according to this embodiment.
Figure 5:
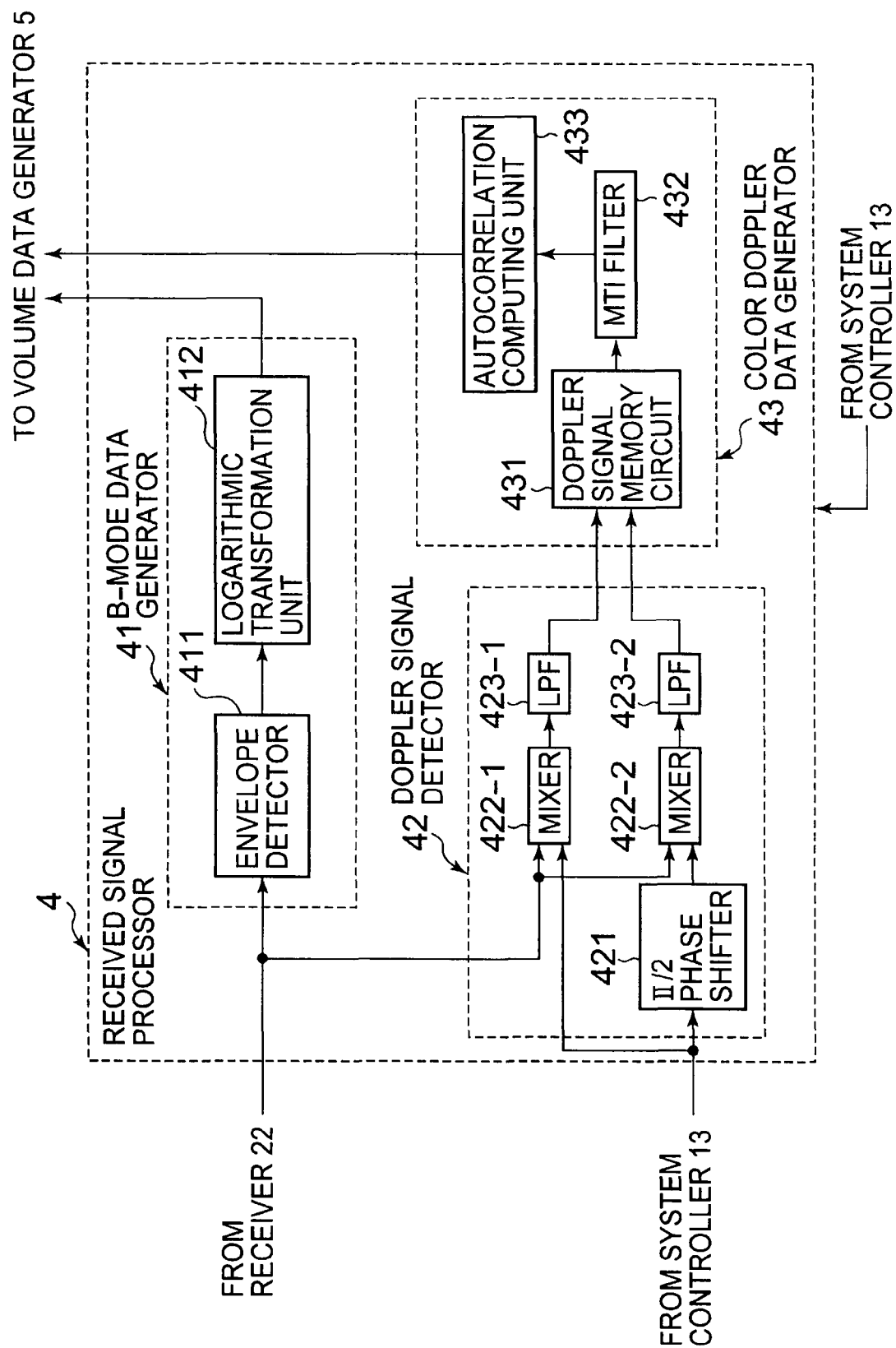
FIG. 5 is a block diagram illustrating a received signal processor of the ultrasound imaging apparatus according to this embodiment.
Figure 6:
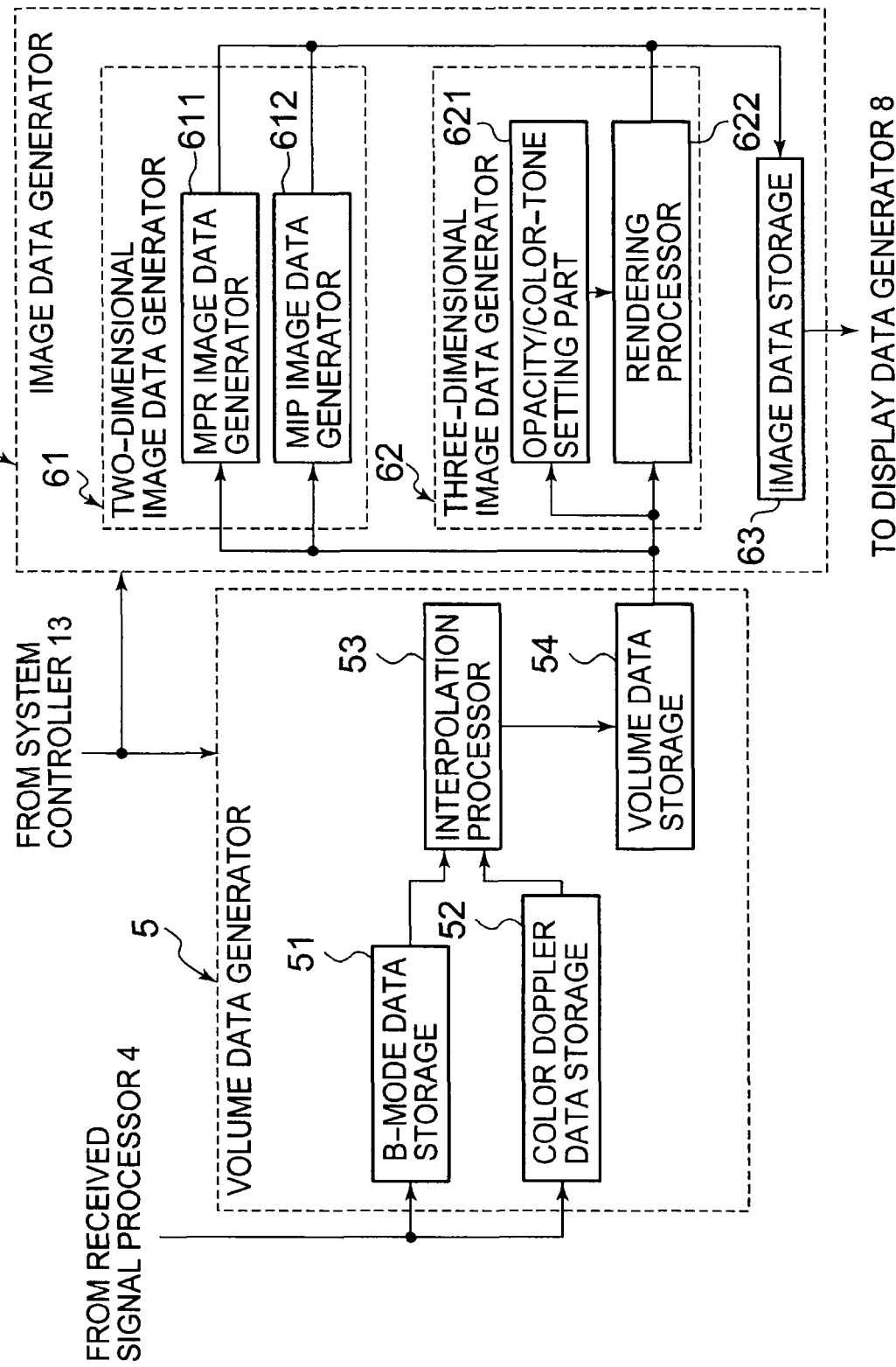
FIG. 6 is a block diagram illustrating a volume data generator and an image data generator of the ultrasound imaging apparatus according to this embodiment.

The ultrasound imaging apparatus according to this embodiment will be described by using FIGS. 1 through 8. FIG. 1 is a block diagram illustrating the entire configuration of the ultrasound imaging apparatus. Moreover, FIGS. 2, 5, and 6 are block diagrams illustrating the detailed configurations of a transceiver, a received signal processor, and a volume data generator and image data generator of this ultrasound imaging apparatus.

An ultrasound imaging apparatus 100 according to this embodiment shown in FIG. 1 includes an ultrasound probe 3, a transceiver 2, a received signal processor 4, and a volume data generator 5. The ultrasound probe 3 includes a plurality of transducers. The plurality of transducers transmit ultrasound pulses (transmitted ultrasound waves) to a three-dimensional region including a treatment target site of a patient, and converts reflected ultrasound waves (received ultrasound waves) acquired from the treatment target site into electric signals (received signals). The transceiver 2 supplies drive signals for transmitting the ultrasound pulses in a predetermined direction of the three-dimensional region, to the transducers of the ultrasound probe 3, and executes phasing addition on received signals of a plurality of channels acquired from these transducers. The received signal processor 4 processes the received signals after the phasing addition, thereby generating B-mode data or color Doppler data. The volume data generator 5 arranges the B-mode data or color Doppler data acquired in the three-dimensional scan on the treatment target site, so as to correspond to the transmission/reception direction of the ultrasound waves, thereby generating three-dimensional data (volume data).

Further, the ultrasound imaging apparatus 100 includes an image data generator 6, a display data generator 8, a display 9, a puncture adapter 10, a scan controller 11, an input part 12, and a system controller 13.

The image data generator 6 generates two-dimensional image data such as MPR (Multi-Planar-Reconstruction) image data and MIP (Maximum Intensity Projection) image data, and three-dimensional image data such as volume rendering image data, based on the abovementioned volume data.

The display data generator 8 generates display data by using the abovementioned various types of image data.

The display 9 displays the display data generated by the display data generator 8.

The puncture adapter 10 is attached to the ultrasound probe 3 to guide the insertion of a puncture needle 15.

The scan controller 11 sets a puncture needle scanning region including the insertion direction of the puncture needle 15 and two treatment target scanning regions adjacent to the puncture needle scanning region, for the relevant treatment target site, and controls three-dimensional scan with ultrasound waves on these scanning regions.

The input part 12 executes input of patient information, setting of conditions for volume data generation, setting of conditions for image data generation, setting of conditions for image data display, setting of slice thicknesses for the puncture needle scanning region and the treatment target scanning regions, setting of a display cross section for volume data, setting of a slab thickness of slab MPR image data or slab MIP image data (described later), input of various command signals, etc.

The system controller 13 comprehensively controls each of the abovementioned units of the ultrasound imaging apparatus 100.

A specific example of each of the units of the ultrasound imaging apparatus 100 according to the present embodiment will be described below.

The ultrasound probe 3 illustrated in FIG. 1 has N pieces of transducers (not illustrated) two-dimensionally arranged at the tip, and each of the transducers is connected to input/output terminals of the transceiver 2 via multicore cables of N channels. The transducer is an electro-acoustic converting element, and has a function of converting electric pulses (drive signals) into ultrasound pulses (transmitted ultrasound waves) in transmission of ultrasound waves and of converting reflected ultrasound waves (received ultrasound waves) into electric received signals in reception of ultrasound waves. Moreover, the puncture adapter 10 is attached to the side of the ultrasound probe 3, for example. The puncture adapter 10 includes a needle guide (not illustrated) that guides the insertion of the puncture needle 15 into the treatment target site. That is to say, it is possible, by inserting the puncture needle 15 along the needle guide of the puncture adapter 10 that is preferable for puncture treatment, to easily set a puncture needle scanning region including the insertion direction of the puncture needle 15.

The ultrasound probe 3 is an ultrasound probe for sector scan, an ultrasound probe for linear scan, an ultrasound probe for convex scan, etc. An operator can select any ultrasound probe depending on a diagnosis site. This embodiment describes use of the ultrasound probe 3 for sector scan in which N pieces of transducers are two-dimensionally arranged.

Subsequently, the transceiver 2 illustrated in FIG. 2 includes a transmitter 21 and a receiver 22. The transmitter 21 supplies drive signals for emitting transmitted ultrasound waves to the patient, to the N pieces of transducers of the ultrasound probe 3. The receiver 22 executes phasing addition (phase-matching and addition) on the received signals of N channels obtained from the transducers.

The transmitter 21 includes a rate pulse generator 211, a transmission delay circuit 212, and a drive circuit 213. The rate pulse generator 211 divides a reference signal supplied from the system controller 13, thereby generating a rate pulse for determining a repetition period of transmitted ultrasound waves. The transmission delay circuit 212 includes an independent delay circuit of N channels. In order to obtain a thin beam width in transmission, the transmission delay circuit 212 gives the rate pulse a delay time (a focus delay time) for focusing transmitted ultrasound waves to a predetermined depth and a delay time (a deflection delay time) for emitting transmitted ultrasound waves in a predetermined transmission/reception direction ($\theta p$, $\phi q$). Then, based on the rate pulse, the independent drive circuit 213 of N channels generates drive pulses for driving the N pieces of transducers embedded in the ultrasound probe 3.

On the other hand, the receiver 22 includes a preamplifier 221, an A/D converter 222, a reception delay circuit 223, which are composed of N channels, and an adder 224. The preamplifier 221 amplifies minute received signals converted into electric signals by the abovementioned transducers, thereby obtaining a sufficient S/N ratio. The received signals of N channels amplified in the preamplifier 221 are converted into digital signals by the A/D converter 222.

The reception delay circuit 223 gives, to each of the received signals of N channels outputted from the A/D converter 222, a focus delay time for focusing reflected ultrasound waves from a predetermined depth and a deflection delay time for setting strong reception directionality for a predetermined transmission/reception direction ($\theta p$, $\phi q$). The adder 224 adds and synthesizes the received signals supplied from the reception delay circuit 223. That is to say, the received signals obtained from a predetermined direction are subjected to phase addition by the reception delay circuit 223 and the adder 224.

Figure 3:
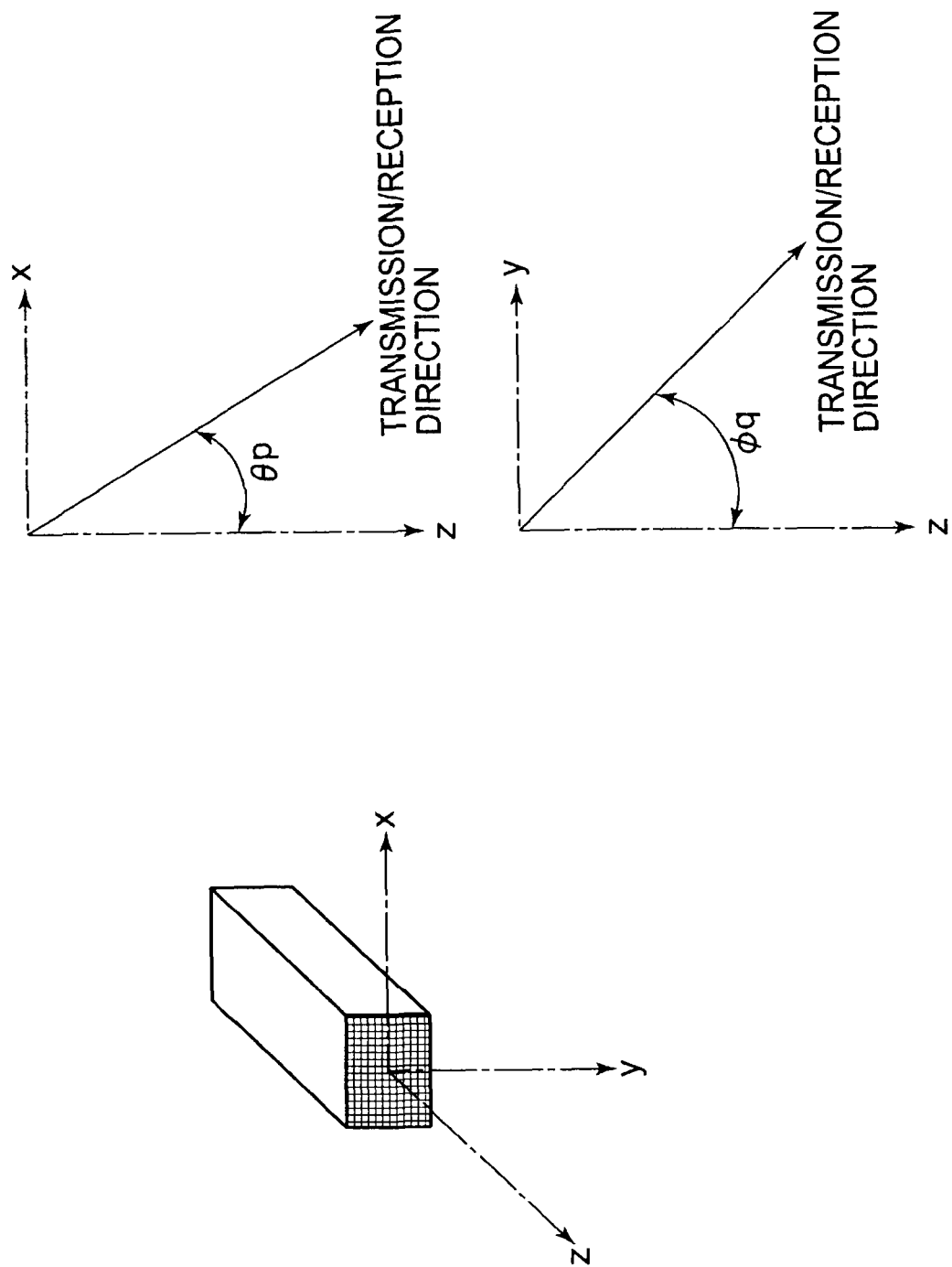
FIG. 3 is a view illustrating the relation between coordinates and a transmission/reception direction in an ultrasound probe according to this embodiment.

FIG. 3 illustrates the relation between the transmission/reception direction ($\theta p$, $\phi q$) of ultrasound waves and the orthogonal coordinate system (x-y-z) in which the central axis of the ultrasound probe 3 is the z-axis. For example, when the N pieces of transducers are two-dimensionally arranged in the x-axis direction and y-axis direction, an angle $\theta p$ indicates the transmission/reception direction projected on the x-z plane, and an angle $\phi q$ indicates the transmission/reception direction projected on the y-z plane.

Then, in accordance with a scan control signal supplied from the scan controller 11, the delay times in the transmission delay circuit 212 of the transmitter 21 and in the reception delay circuit 223 of the receiver 22 is controlled, and three-dimensional scan is repeatedly executed on the puncture needle scanning region and the treatment target scanning regions at different frequencies.

Next, a puncture needle scanning region and treatment target scanning regions set in a three-dimensional region of the relevant patient will be described with FIG. 4.

In this case, in a three-dimensional region including a treatment target site 150, a region with a slice thickness d1 including the insertion direction of the puncture needle 15 inserted along the needle guide (not illustrated) is firstly set as a puncture needle scanning region R1. Subsequently, in the y-direction substantially perpendicular to the central cross section (slab cross section) of the puncture needle scanning region R1, two treatment target scanning regions R2 (treatment target scanning regions R21 and R22) each having a slice thickness d2 and adjacent to the puncture needle scanning region R1 are set.

More specifically, with observation of image data (e.g., two-dimensional image data or three-dimensional image data described later) acquired with three-dimensional scan on the puncture needle scanning region R1, the position and direction of the ultrasound probe 3 are adjusted on the body surface of the patient so that the puncture position on the treatment target site 150 and the insertion direction of the puncture needle 15 coincide with each other. The puncture needle scanning region R1 for the treatment target site 150 is set as a result of the adjustments.

Then, for three-dimensional scan on the abovementioned puncture needle scanning region R1 and treatment target scanning regions R2, in the puncture needle scanning region R1 in which the puncture needle 15 is inserted into the treatment target site 150, three-dimensional scan is executed at a higher volume rate (temporal resolution) than in the treatment target scanning regions R2.

The received signal processor 4 shown in FIG. 5 includes a B-mode data generator 41, a Doppler signal detector 42, and a color Doppler data generator 43. The B-mode data generator 41 processes received signals outputted from the adder 224 of the receiver 22, thereby generating B-mode data. The Doppler signal detector 42 executes quadrature detection on the received signals, thereby detecting Doppler signals. The color Doppler data generator 43 generates, based on the detected Doppler signals, color Doppler data that reflects blood flow information within the blood vessels.

The B-mode data generator 41 includes an envelope detector 411 and a logarithmic transformation unit 412. The envelope detector 411 detects an envelope curve of the received signals after phase addition supplied from the adder 224 of the receiver 22. The logarithmic transformation unit 412 executes logarithmic transformation on the received signals after the envelope curve has been detected, thereby generating B-mode data. The envelope detector 411 and the logarithmic transformation unit 412 may be switched in order.

The Doppler signal detector 42 includes a $\pi/2$ phase shifter 421, mixers 422-1 and 422-2, and LPFs (Low Pass Filters) 423-1 and 423-2. The Doppler signal detector 42 executes quadrature detection on the received signals supplied from the adder 224 of the receiver 22, thereby detecting Doppler signals.

The color Doppler data generator 43 includes a Doppler signal memory circuit 431, an MTI filter 432, and an autocorrelation computing unit 433. The Doppler signal memory circuit 431 temporarily stores Doppler signals detected by the Doppler signal detector 42. The MTI filter 432 eliminates Doppler signal components (clutter components) attributable to movement of living body tissue or the like included in the Doppler signals, and extracts Doppler signal components attributable to a blood flow. The autocorrelation computing unit 433 executes autocorrelation computation on the extracted Doppler signal components, and generates color Doppler data by using characteristic values (e.g., average speed value, variance value, and power value of blood flow) obtained based on the result of the computation.

Next, a detailed configuration of the volume data generator 5 and the image data generator 6 shown in FIG. 1 will be described with reference to FIG. 6. The volume data generator 5 includes a B-mode data storage 51, a color Doppler data storage 52, an interpolation processor 53, and a volume data storage 54 as shown in FIG. 6.

The B-mode data storage 51 stores B-mode data generated by the B-mode data generator 41 of the received signal processor 4 based on received signals obtained by three-dimensional scan on the puncture needle scanning region R1 and the treatment target scanning regions R2 of the relevant patient, with the transmission/reception direction of the ultrasound waves as additional information. Similarly, the color Doppler data storage 52 stores color Doppler data generated by the color Doppler data generator 43 of the received signal processor 4 based on received signals is stored with the transmission/reception direction as additional information.

On the other hand, the interpolation processor 53 arranges a plurality of B-mode data read out from the B-mode data storage 51 so as to correspond to the transmission/reception direction, thereby forming three-dimensional B-mode data of the puncture needle scanning region R1 and the treatment target scanning regions R2. Furthermore, the interpolation processor 53 executes an interpolation process on unequally spaced voxels composing the three-dimensional B-mode data, thereby generating B-mode volume data composed of isotropic voxels.

Similarly, the interpolation processor 53 arranges a plurality of color Doppler data read out from the color Doppler data storage 52 so as to correspond to the transmission/reception direction, thereby forming three-dimensional color Doppler data of the puncture needle scanning region R1 and the treatment target scanning regions R2. Furthermore, the interpolation processor 53 executes an interpolation process on the three-dimensional color Doppler data, thereby generating Doppler mode volume data. Then, the volume data obtained from the puncture needle scanning region R1 and the treatment target scanning regions R2 are temporarily stored into the volume data storage 54.

In this embodiment, three-dimensional scan is repeatedly executed on the puncture needle scanning region R1 and the treatment target scanning regions R2 at different frequencies. The former volume data in the same scanning region that has already been acquired is updated to the latest volume data acquired at this time. The details of this update will be described later.

The image data generator 6 includes a two-dimensional image data generator 61 and a three-dimensional image data generator 62. In addition, the two-dimensional image data generator 61 includes an MPR image data generator 611 and an MIP image data generator 612.

The MPR image data generator 611 generates two types of display images, i.e., MPR image data and slab MPR image data, based on volume data in the puncture needle scanning region R1 and the treatment target scanning regions R2 supplied by the volume data storage 54 of the volume data generator 5 and based on information on a display cross section set by the input part 12.

In this case, the MPR image data is image data generated by interpolating the voxel values on the set display cross section or proximal voxel values, and is image data in which the thickness is regarded as zero.

Moreover, the slab MPR image data has a predetermined thickness (slab thickness) set for the above MPR image data, and is image data generated, centered on the display cross section set in the volume data from the puncture needle scanning region R1 and the treatment target scanning regions R2, based on the average value of a plurality of voxel values within the above slab thickness in the normal direction of the display cross section.

On the other hand, the MIP image data generator 612 generates slab MIP image data based on the puncture needle scanning region R1 and the treatment target scanning regions R2 and based on the information on the display cross section set by the input part 12. In this case, the slab MIP image data is image data generated, centered on the display cross section set in the volume data from the puncture needle scanning region R1 and the treatment target scanning regions R2, based on the maximum value of a plurality of voxel values within the above slab thickness in the normal direction of the display cross section.

The three-dimensional image data generator 62 includes an opacity/color-tone setting part 621 and a rendering processor 622. The opacity/color-tone setting part 621 sets the opacity and color tone based on a voxel value in the volume data from the puncture needle scanning region R1 and the treatment target scanning regions R2 supplied by the volume data storage 54 of the volume data generator 5.

On the other hand, the rendering processor 622 executes a rendering process on the abovementioned volume data based on information on the opacity and color tone set by the opacity/color-tone setting part 621, thereby generating three-dimensional image data such as volume rendering image data and surface rendering image data. The two-dimensional image data such as MPR image data, slab MPR image data and slab MIP image data generated in the two-dimensional image data generator 61 and three-dimensional image data generated in the three-dimensional image data generator 62 are stored into the image data storage 63.

With reference to FIG. 1 again, the display data generator 8 will be described. The display data generator 8 executes coordinate transformation and synthesis based on a predetermined display format, on slab MPR image data (or slab MIP image data) and MPR image data generated in the two-dimensional image data generator 61 of the image data generator 6 and on three-dimensional image data generated in the three-dimensional image data generator 62, and then superimposes additional information such as patient information, thereby generating display data. Meanwhile, the display 9 includes a conversion circuit and a monitor, which are not shown. The conversion circuit executes D/A conversion and television format conversion on the abovementioned display data generated in the display data generator 8, and displays on the monitor.

Figure 7A:
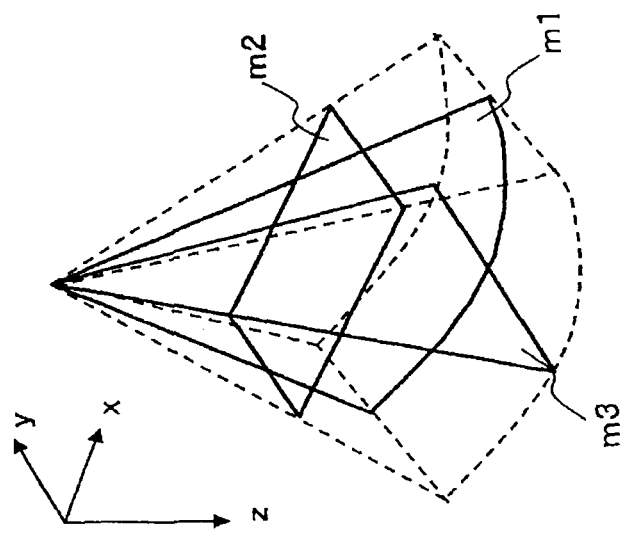
FIG. 7A is a view illustrating cross sections from which image data is generated.
Figure 7B:
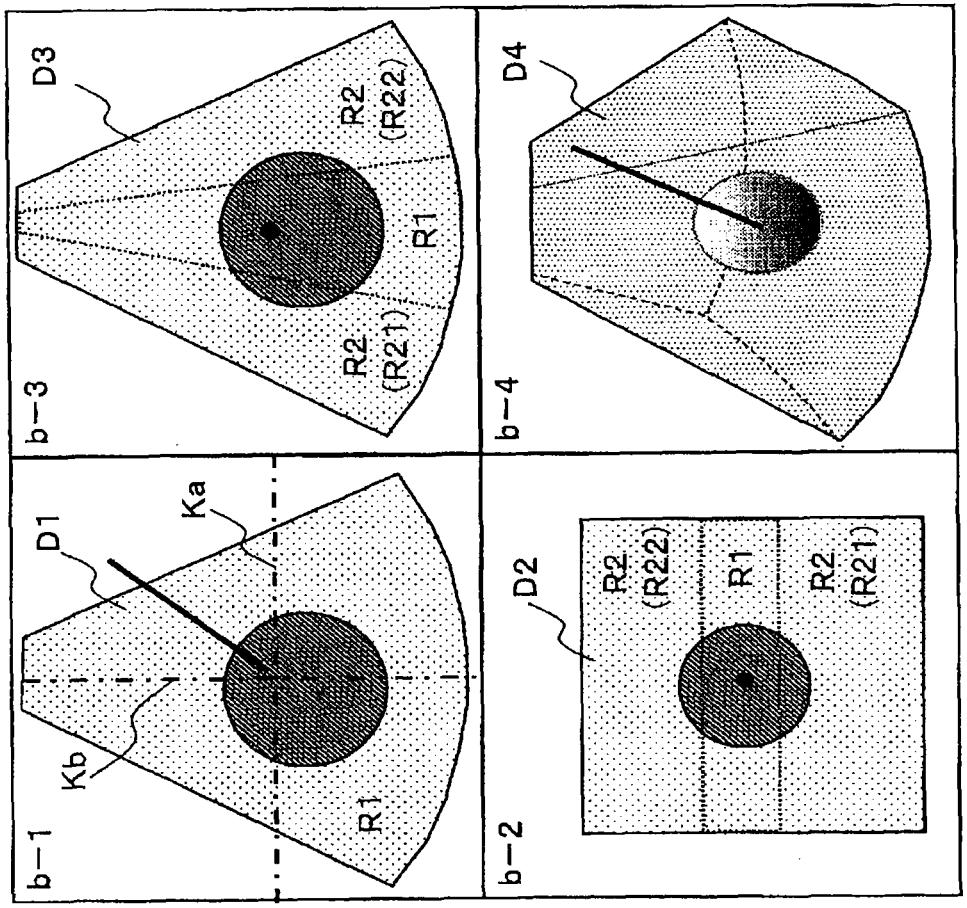
FIG. 7B is a view illustrating a specific example of display data generated by a display data generator according to this embodiment.

FIGS. 7A and 7B are views for describing a specific example of the display data generated in the display data generator 8 and displayed on the display 9. However, the two-dimensional image data displayed as a specific example here will be MPR image data. For example, FIG. 7A illustrates a display cross section m1 of the puncture needle scanning region R1 on which MPR image data substantially perpendicular to the y-direction is generated, a display cross section m2 of the puncture needle scanning region R1 and the treatment target scanning regions R2 on which MPR image data substantially perpendicular to the z-direction is generated, and a display cross section m3 of the puncture needle scanning region R1 and the treatment target scanning regions R2 on which MPR image data substantially perpendicular to the x-direction is generated.

On the other hand, in a region (b-1) shown in FIG. 7B, slab MPR image data D1 generated by the two-dimensional image data generator 61 of the image data generator 6 for the display cross section m1 shown in FIG. 7A is shown. Moreover, in a region (b-2), MPR image data D2 generated by the two-dimensional image data generator 61 for the display cross section m2 is shown. Moreover, in a region (b-3), MPR image data D3 generated by the two-dimensional image data generator 61 for the display cross section m3 is shown. Moreover, in a region (b-4), three-dimensional image data D4 generated by the three-dimensional image data generator 62 based on the volume data of the puncture needle scanning region R1 and the treatment target scanning regions R2 is shown. In MPR image data D1 shown in the region (b-1), a cursor Ka indicating the cross-section position of MPR image data D2 and a cursor Kb indicating the cross-section position of MPR image data D3 set by the input part 12 are superimposed. Then, the display data generator 8 generates display data by synthesizing the MPR image data D1, the MPR image data D2, the MPR image data D3, and the three-dimensional image data D4 based on predetermined display formats.

In other words, the operator having observed the MPR image data D1 of the display data shown on the display 9 operates a display cross section setting part 122 (described later) of the input part 12 to move the cursor Ka and the cursor Kb superimposed on the MPR image data D1 to desired positions, thereby setting the position of the MPR image data (an MPR cross section). Then, the MPR image data D2 in the display cross section m2 set by the cursor Ka and the MPR image data D3 in the display cross section m3 set by the cursor Kb are displayed in the region (b-2) and the region (b-3) shown in FIG. 7B, respectively.

Although FIGS. 7A and 7B describe the setting of a display cross section using MPR image data substantially perpendicular to the y-direction generated based on volume data of the puncture needle scanning region R1, an MPR cross section may be set by using slab MPR image data or slab MIP image data, instead of MPR image data.

On the other hand, the scan controller 11 shown in FIG. 1 sets, based on the slice thickness d1 of the puncture needle scanning region R1 and the slice thicknesses d2 of the treatment target scanning regions R2 set by the input part 12, the puncture needle scanning region R1 and the treatment target scanning regions R2 for the relevant treatment target site 150 (refer to FIG. 4), and executes control for repeating three-dimensional scan on these scanning regions in a predetermined order.

Next, a specific example of three-dimensional scan on the puncture needle scanning region R1 and the treatment target scanning regions R2 that is executed under control of the scan controller 11 will be described with reference to FIG. 8.

FIG. 8 is a time chart illustrating the order of three-dimensional scans on the puncture needle scanning region R1 and the two treatment target scanning regions R2 (i.e., the treatment target scanning regions R21 and R22) and the update timing of volume data accompanying these three-dimensional scans. A mark ∇ in the figure indicates the update timing of volume data in the treatment target scanning regions R2. A mark ▼ indicates the update timing of volume data in the puncture needle scanning region R1.

For example, during a time period [t10-t11], three-dimensional scans are sequentially executed on the treatment target scanning region R21, the puncture needle scanning region R1 and the treatment target scanning region R22. Then, volume data in the respective scanning regions are generated (updated) based on received signals obtained during this time period, and two-dimensional image data and three-dimensional image data are generated and displayed by using these volume data (refer to FIG. 7).

Next, during a time period [t11-t12], three-dimensional scan is executed on the puncture needle scanning region R1 and, by using volume data newly obtained during this time period, the volume data of the puncture needle scanning region R1 obtained in the time period [t10-t11] is updated.

Then, two-dimensional image data and three-dimensional image data are generated and displayed by using the volume data of the treatment target scanning regions R21 and R22 acquired during the time period [t10-t11] and the volume data of the puncture needle scanning region R1 updated during the time period [t11-t12] in the same procedure.

In the same manner, three-dimensional scan is executed on the puncture needle scanning region R1 during time periods [t12-t13], [t13-t14] and [t14-t20], whereby the volume data of the puncture needle scanning region R1 is sequentially updated. Then, two-dimensional image data and three-dimensional image data are generated and displayed repeatedly by using the volume data of the treatment target scanning regions R21 and R22 acquired during the time period [t10-t11] and the volume data of the puncture needle scanning region R1 updated during each of the abovementioned time periods.

The three-dimensional scan and the generation and display of image data during a time period [t10-t20] described above are repeated in the same procedure during time periods [t20-t30], [t30-t40], and so forth. In this scanning method, the volume data of the puncture needle scanning region R1 is updated at higher frequency (flame rate) than those of the treatment target scanning regions R2. Thus, it is possible to observe the state of the puncture needle 15 inserted into the treatment target site 150 with excellent temporal resolution.

The input part 12 shown in FIG. 1 is an interactive interface provided with a display panel and an input device such as a keyboard, various switches, a selection button and a mouse. The input part 12 includes a slice thickness setting part 121 and a display cross section setting part 122. The slice thickness setting part 121 sets the slice thickness d1 of the puncture needle scanning region R1 and the slice thicknesses d2 of the treatment target scanning regions R2. The display cross section setting part 122 sets a display cross section for MPR image data, slab MPR image data, or slab MIP image data. Furthermore, input of patient information, setting of conditions for volume data generation, setting of conditions for image data generation, setting of conditions for image data display, input of various command signals, etc. are executed by using the display panel and the input device.

The system controller 13 includes a CPU (Central Processing Unit) and a memory circuit, which are not shown. The memory circuit stores the abovementioned various types of information inputted/set by the respective units of the input part 12. Based on the abovementioned input information and setting information, the CPU controls the respective units of the ultrasound imaging apparatus 100, and generates and displays image data.

(Procedure for Generating/Displaying Image Data)

Next, the procedure for generating/displaying image data for the purpose of supporting puncture in this embodiment will be described with reference to a flow chart shown in FIG. 9 and the time chart shown in FIG. 8.

Although MPR image data will be generated as two-dimensional image data in the display cross section m1 of the puncture needle scanning region R1 in this description, slab MPR image data or ordinary slab MIP image data may be generated.

Figure 9:
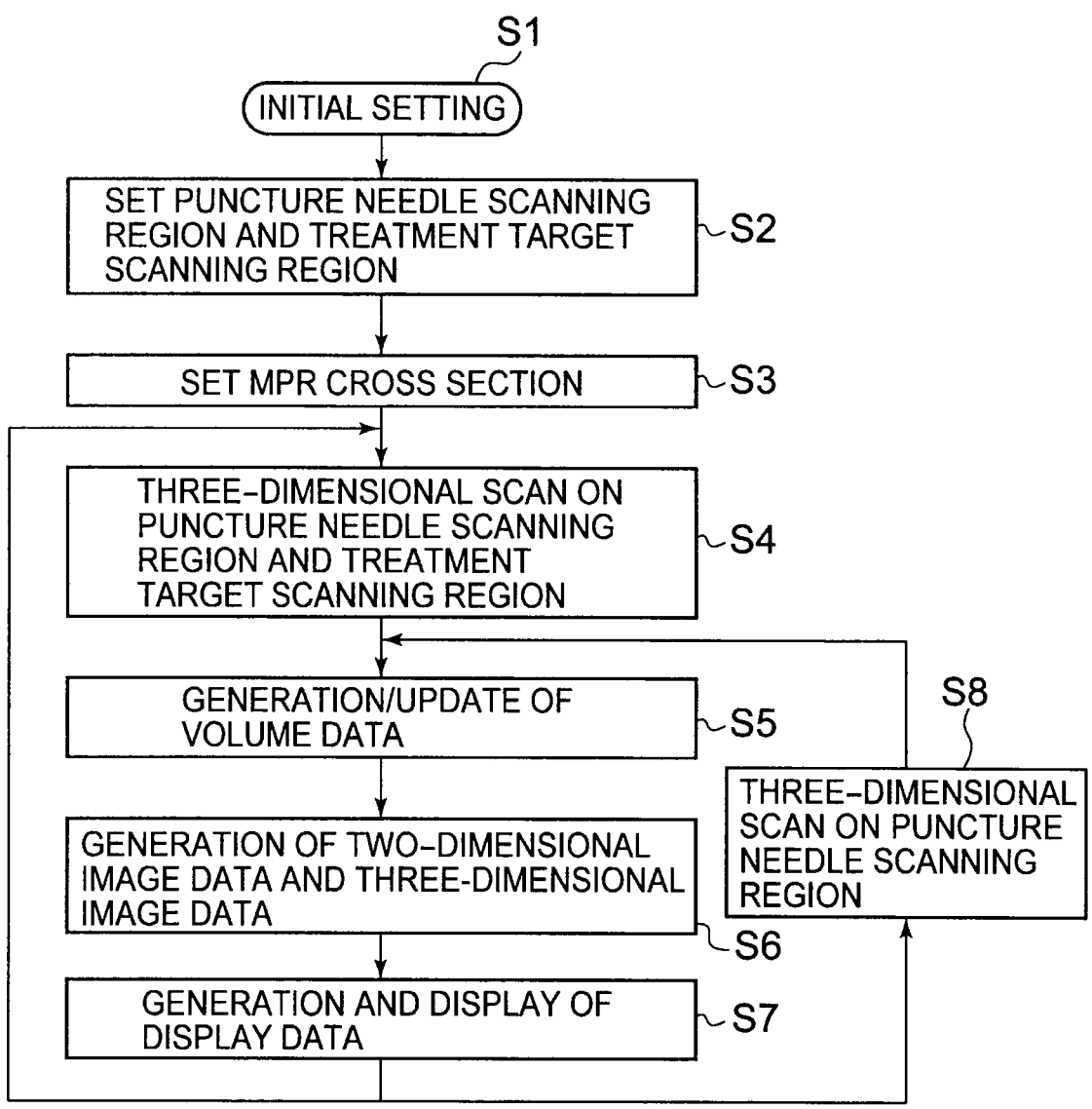
FIG. 9 is a flow chart illustrating the procedure for the steps for generating image data and displaying an image for the purpose of supporting puncture in the ultrasound imaging apparatus according to this embodiment.

Prior to generation of image data for the purpose of supporting puncture, the operator of the ultrasound imaging apparatus 100 executes input of patient information, setting of conditions for volume data generation, setting of conditions for image data generation, setting of conditions for image data display, setting of the slice thickness d1 of the puncture needle scanning region R1, setting of the slice thicknesses d2 of the treatment target scanning regions R2, etc., by using the input part 12, and thereafter, places the ultrasound probe 3 on the body surface of the patient and inputs a first command to start image data generation for the purpose of setting a scanning region and a display cross section (Step S1 in FIG. 9).

Figure 4:
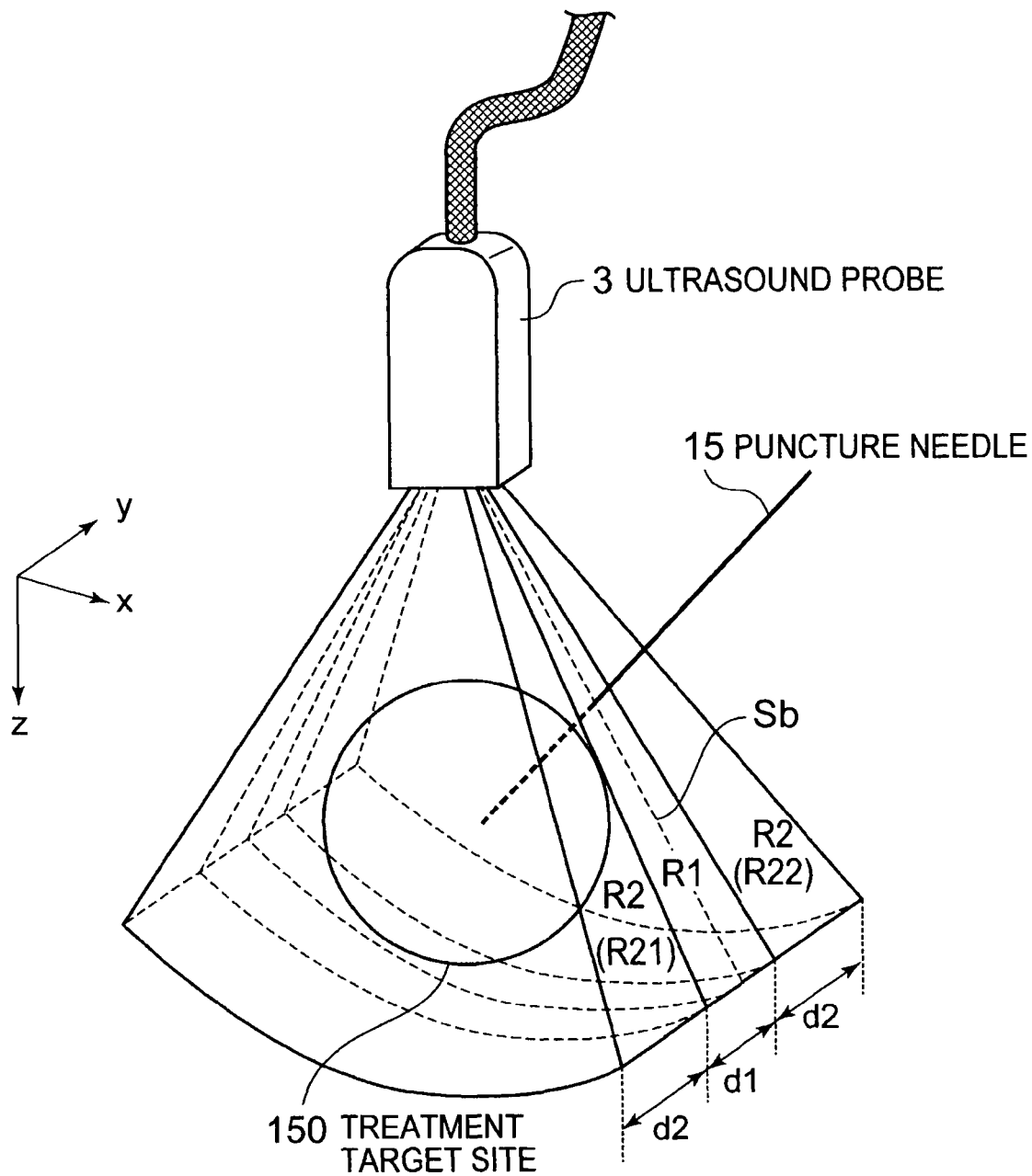
FIG. 4 is a view illustrating treatment target scanning regions and a puncture needle scanning region according to this embodiment.

The scan controller 11 having received the first command to start image data generation via the system controller 13 sets the puncture needle scanning region R1 including the insertion direction of the puncture needle 15 and having the slice thickness d1, and the two treatment target scanning regions R2 (the treatment target scanning regions R21 and R22) adjacent to the puncture needle scanning region R1 and having the slice thicknesses d2 (refer to FIG. 4). Moreover, the scan controller 11 controls delay times in the transmission delay circuit 212 and the reception delay circuit 223 of the transceiver 2, and starts three-dimensional scan on the puncture needle scanning region R1.

On the other hand, the operator adjusts the position and direction of the ultrasound probe 3 on the body surface of the patient, with observation of MPR image data generated by the three-dimensional scan on the puncture needle scanning region R1. The position and direction of the ultrasound probe 3 are fixed in a state that a puncture marker indicating the insertion direction of the puncture needle 15 superimposed and displayed on the abovementioned MPR image data coincides with the insertion position into the treatment target site 150, whereby the abovementioned puncture needle scanning region R1 and the treatment target scanning regions R2 are set for the relevant treatment target site 150 (Step S2 in FIG. 9).

Furthermore, the operator moves the cursor Ka and the cursor Kb superimposed and displayed on the abovementioned MPR image data to desired positions by using the display cross section setting part 122 of the input part 12 (refer to FIG. 7B), thereby setting the display cross section m2 and the display cross section m3 for the treatment target site 150 (Step S3 in FIG. 9).

When the setting of the puncture needle scanning region R1 and the treatment target scanning regions R2 for the treatment target site 150 and the setting of the display cross sections m2 and m3 are completed, the operator inputs a second command to start image data generation for the purpose of supporting treatment by using the input part 12. The scan controller 11 having received the second command to start image data generation via the system controller 13 controls delay times in the transmission delay circuit 212 and the reception delay circuit 223 of the transceiver 2. For example, the scan controller 11 sequentially executes three-dimensional scans on the treatment target scanning region R21, the puncture needle scanning region R1 and the treatment target scanning region R22 during the time period [t10-t11] of FIG. 8 (Step S4 in FIG. 9).

On the other hand, the volume data generator 5 generates volume data of the puncture needle scanning region R1 and the treatment target scanning regions R2 based on the received signals obtained by the abovementioned three-dimensional scans (Step S5 in FIG. 9).

The image data generator 6 processes these volume data to generate the MPR image data D1 in the display cross section m1 of the puncture needle scanning region R1, the MPR image data D2 in the display cross section m2 set on the puncture needle scanning region R1 and the treatment target scanning regions R2, the MPR image data D3 in the display cross section m3 set on the puncture needle scanning region R1 and the treatment target scanning regions R2, and the three-dimensional image data D4 in the puncture needle scanning region R1 and the treatment target scanning regions R2 (Step S6 in FIG. 9).

Subsequently, the display data generator 8 generates display data by using these image data, and displays on the monitor of the display 9 (Step S7 in FIG. 9).

Next, the scan controller 11 controls delay times in the transmission delay circuit 212 and the reception delay circuit 223 during the time period [t11-t12] to execute three-dimensional scan on the puncture needle scanning region R1 (Step S8 in FIG. 9) and, by using the volume data newly obtained during this time period, updates the volume data of the puncture needle scanning region R1 acquired during the time period [t10-t11] (Step S5 in FIG. 9).

Then, two-dimensional image data and three-dimensional image data are generated and displayed by using the volume data of the treatment target scanning regions R2 acquired during the time period [t10-t11] and the volume data of the puncture needle scanning region R1 updated during the time period [t11-12] in the same procedure (Step S6 and Step S7 in FIG. 9).

Similarly, a three-dimensional scan is executed on the puncture needle scanning region R1 during the time periods [t12-t13], [t13-t14] and [t14-t20], whereby the volume data of the puncture needle scanning region R1 is sequentially updated. Then, two-dimensional image data and three-dimensional image data are generated and displayed by using the volume data of the treatment target scanning regions R2 acquired during the time period [t10-t11] and the volume data of the puncture needle scanning region R1 updated in each of the abovementioned time periods (Step S5 through Step S8 in FIG. 9).

Furthermore, the three-dimensional scan and the generation and display of image data as in the time period [t10-t20] are repeatedly executed during the time periods [t20-t30], [t30-t40], and so forth (Step S4 through Step S8 in FIG. 9).

According to the embodiment of the present invention described above, when inserting a puncture needle into the patient with observation of the image data acquired by the three-dimensional scan with ultrasound waves, it is possible to almost simultaneously observe image data in the treatment target scanning regions and image data in the puncture needle scanning region that is better in temporal resolution than the former image data. Thus, accurate insertion of a puncture needle into the treatment target site is facilitated, the safety and efficiency in puncture treatment are increased, and the burden on the operator and the patient is reduced.

In particular, MPR image data, slab MPR image data or slab MIP image data in a desired cross section generated based on volume data acquired by a three-dimensional scan and three-dimensional image data are almost simultaneously displayed, and information on the puncture needle scanning region in these image data are updated at high volume rate, so that it is possible to accurately grasp the state of the puncture needle inserted into the treatment target site.

The embodiment of the present invention has been described above.

The present invention is not limited to the abovementioned embodiment and can be modified and implemented. For example, the above embodiment describes a case that, as shown in FIG. 4, a cross section including the insertion direction of the puncture needle 15 is a puncture cross section Sb and the puncture needle scanning region R1 and the treatment target scanning regions R2 having predetermined slice thicknesses are set with reference to the puncture cross section Sb. Alternatively, as shown in FIG. 10A, the puncture needle scanning region R1 may be set with reference to a cross section substantially perpendicular to the insertion direction of the puncture needle 15, and the two treatment target scanning regions R2 adjacent to the puncture needle scanning region R1 in the insertion direction may be set. In this case, in slab MPR image data or slab MIP image data shown in the region (b-1) in FIG. 10B, the position of the puncture needle 15 inserted into the treatment target site 150 is displayed as a dot. Therefore, it is possible to more accurately grasp the insertion position into the treatment target site 150.

The method for the three-dimensional scan on the puncture needle scanning region R1 and the treatment target scanning regions R2 is not limited to the method shown in FIG. 8 and, for example, may be methods shown in FIGS. 11A and 11B. For example, as shown in FIG. 11A, the treatment target scanning regions R2 (the treatment target scanning regions R21 and R22) are scanned once and the puncture needle scanning region R1 is scanned plural times, and thereafter, the scans on the treatment target scanning regions R2 and the puncture needle scanning region R1 are continued. By thus scanning the puncture needle scanning region R1 more frequently than the treatment target scanning regions R2, it is possible to scan the puncture needle scanning region R1 at a higher volume rate. This enables generation of image data in the puncture needle scanning region R1 that is excellent in temporal resolution.

Alternatively, as shown in FIG. 11B, the treatment target scanning region R21 (or the treatment target scanning region R22) and the puncture needle scanning region R1 are alternately scanned in the order of the treatment target scanning region R21, the puncture needle scanning region R1, the treatment target scanning region R22, the puncture needle scanning region R1, and so forth. Particularly in the method shown in FIG. 11B, three-dimensional scan on the puncture needle scanning region R1 is executed at equal time intervals, though it is impossible to largely increase the volume rate. Thus, it is possible to observe the puncture needle 15 showing a smooth movement, in two-dimensional image data and three-dimensional image data acquired by the three-dimensional scan.

The scanning-line densities in the puncture needle scanning region R1 and the treatment target scanning regions R2 are not particularly referred to in the abovementioned embodiment. As already described, the object of the present invention is to accurately grasp the state of the puncture needle 15 inserted into the treatment target site 150. In other words, two-dimensional image data and three-dimensional image data with excellent temporal resolution and spatial resolution are required for the puncture needle scanning region R1 on which the puncture needle 15 is displayed. Thus, the scan controller 11 is required to control so as to three-dimensionally scan the puncture needle scanning region R1 at higher scanning-line density and higher volume rate than the treatment target scanning regions R2. Although the abovementioned scanning-line density and volume rate (i.e., temporal resolution) are generally in a trade-off relation, it is possible, by setting the puncture needle scanning region R1 narrow, to easily realize the three-dimensional scan on the treatment target site 150 that simultaneously satisfies these requirements.

Figure 12:
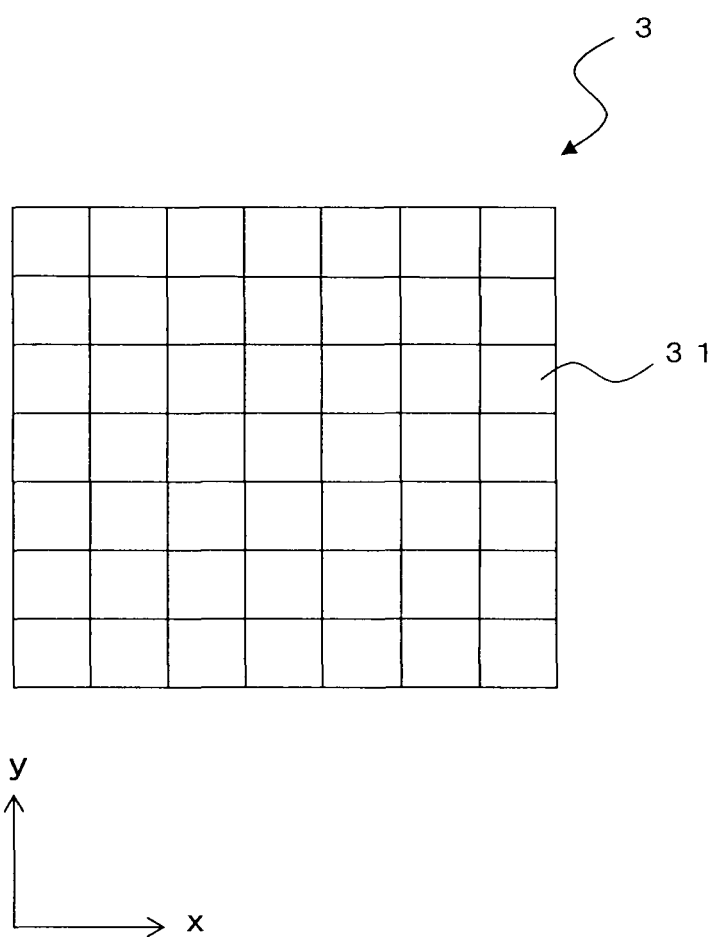
FIG. 12 is a view illustrating the arrangement of transducers in an ultrasound probe compatible with a sector scan of the ultrasound imaging apparatus according to this embodiment.
Figure 13:
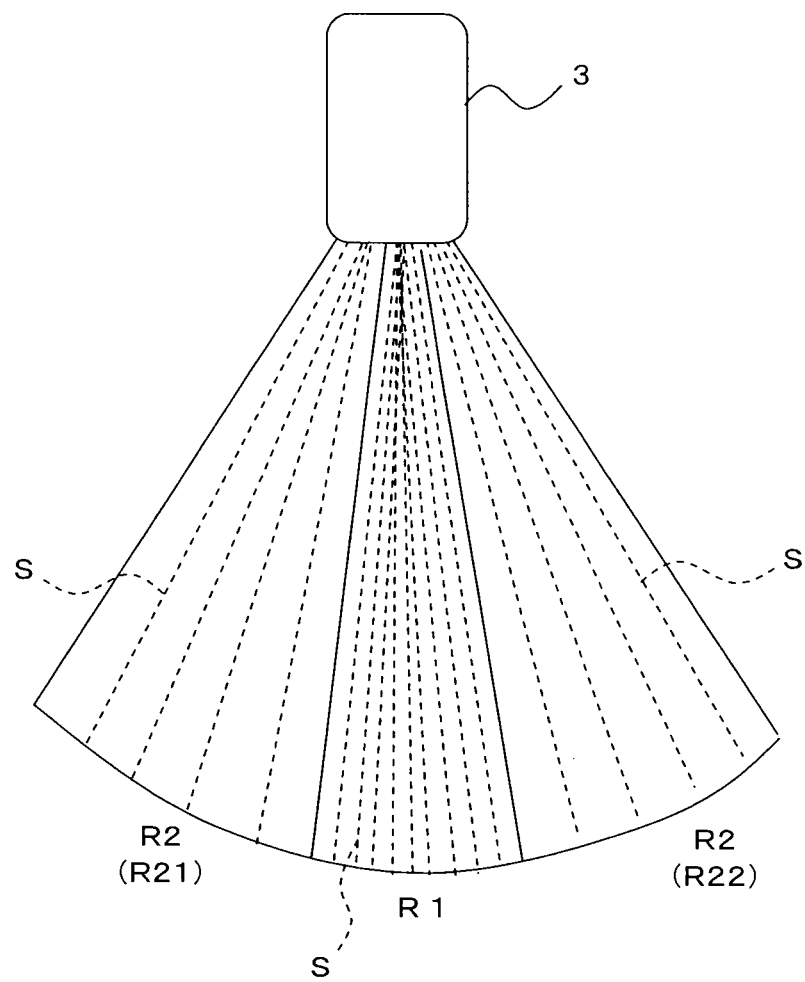
FIG. 13 is a view illustrating the density of scanning lines of ultrasound waves in a puncture needle scanning region and treatment target scanning regions.

As an example, setting of spatial resolution when using an ultrasound probe compatible with sector scan as the ultrasound probe 3 will be described with reference to FIGS. 12 and 13. In a plan view of FIG. 12, the arrangement of the transducers 31 in the ultrasound probe 3 compatible with sector scan is shown. For example, in the ultrasound probe 3 compatible with sector scan, the plurality of transducers 31 having the same shapes and same sizes are arranged two-dimensionally at equal intervals on the x-y plane.

When this ultrasound probe 3 compatible with sector scan is used, the scan controller 11 controls the transceiver 2 to execute three-dimensional scan on the puncture needle scanning region R1 at higher scanning-line density than on the treatment target scanning regions R2. For example, as shown in FIG. 13, the scan controller 11 three-dimensionally scans the puncture needle scanning region R1 and the treatment target scanning regions R2 in a state that the density of the scanning lines S (the number of the scanning lines S per unit volume) in the puncture needle scanning region R1 is higher than the density of the scanning lines S in the treatment target scanning regions R2 (the treatment target scanning regions R21 and R22). By thus three-dimensionally scanning in a state that the density of the scanning lines S in the puncture needle scanning region R1 is higher, it is possible to generate two-dimensional image data and three-dimensional image data with excellent spatial resolution.

As described above, the three-dimensional scans on the puncture needle scanning region R1 and the treatment target scanning regions R2 and the update of volume data are executed at the timings in accordance with the time chart shown in FIG. 8, 11A or 11B. Thus, by executing the three-dimensional scans and the update of volume data in accordance with the time chart shown in FIG. 8 or the like and executing the three-dimensional scans in a state that the scanning-line density in the puncture needle scanning region R1 is higher than in the treatment target scanning regions R2, it is possible to generate two-dimensional image data and three-dimensional image data in the puncture needle scanning region R1 with excellent temporal resolution and spatial resolution.

Moreover, in a case that an ultrasound probe compatible with convex scan or linear scan is used as the ultrasound probe 3, spatial resolution in the puncture needle scanning region R1 is enhanced by the arrangement of the transducers. An example of the arrangement of the transducers is shown in FIG. 14. In a plan view of FIG. 14, the arrangement of the transducers 31 in the ultrasound probe 3 compatible with convex scan or linear scan is shown.

For example, the transducers 31 are two-dimensionally arranged on a two-dimensional x-y plane so that the density of the transducers 31 (the number of transducers 31 per unit area) in a position corresponding to the puncture needle scanning region R1 is higher than the density of the transducers 31 (the number of transducers 31 per unit area) in a position corresponding to the treatment target scanning regions R2 (the treatment target scanning regions R21 and R22). As an example, in a state that, among the plurality of transducers 31 arranged on the x-y plane, the density of the transducers 31 in the middle position corresponding to the puncture needle scanning region R1 is higher than the density of the transducers 31 in the position corresponding to the two treatment target scanning regions R21 and R22 adjacent to the puncture needle scanning region R1, the plurality of transducers 31 are arranged. Further, in the example shown in FIG. 14, the plurality of transducers 31 are arranged in a state that the size of the transducers 31 in the position corresponding to the puncture needle scanning region R1 is smaller than the size of the transducers 31 in the position corresponding to the treatment target scanning regions R2.

Use of the ultrasound probe 3 compatible with convex scan or linear scan shown in FIG. 14 makes it possible to, in the puncture needle scanning region R1 with higher arrangement density of the transducers 31, generate two-dimensional image data and three-dimensional image data with higher spatial resolution than in the treatment target scanning regions R2.

Also when the ultrasound probe 3 compatible with convex scan or linear scan is used, the three-dimensional scan and the update of volume data are executed at the timings in accordance with the time chart shown in FIG. 8, 11A or 11B as described above. By thus executing the three-dimensional scan and the update of the volume data in accordance with the time chart shown in FIG. 8 or the like and executing the three-dimensional scan in a state that the density of transducers 31 in the position corresponding to the puncture needle scanning region R1 is higher, it is possible to generate two-dimensional image data and three-dimensional image data in the puncture needle scanning region R1 with excellent temporal resolution and spatial resolution.

Further, although, among the plurality of transducers 31 arranged two-dimensionally, the density of the transducers 31

(the number of the transducers 31 per unit area) in the central region is higher in the example shown in FIG. 14, a region where the density of the transducers 31 is high may be changed in association with the position of the puncture needle scanning region R1. For example, among the plurality of transducers 31 arranged two-dimensionally, the density of the transducers 31 in a region near the edge may be higher. Moreover, even if the density of the transducers 31 in the central region is higher as shown in FIG. 14, it is possible to deflect the ultrasound beam to transmit and receive, thereby generating image data with excellent spatial resolution for a region with an angle with respect to the ultrasound probe 3.

The above embodiment describes a case in which the puncture needle scanning region R1 and the two treatment target scanning regions R21 and R22 adjacent to the puncture needle scanning region R1 are set. Alternatively, only one of the treatment target scanning regions may be used, or the treatment target scanning regions R21 and R22 may have different slice thicknesses. Furthermore, although the slice thickness of the puncture needle scanning region R1 and the slice thicknesses of the treatment target scanning regions R21 and R22 are set by the slice thickness setting part 121 of the input part 12 in the above description, slice-thickness data previously stored in the memory circuit or the like of the system controller 13 may be used.

Further, although volume data is generated by using B-mode data and color Doppler data in the above description, volume data may be generated by using either the B-mode data or the color Doppler data or using other ultrasound data. Furthermore, although an ultrasound diagnosis for supporting puncture treatment is described above, the ultrasound imaging apparatus may be for supporting examination using the puncture needle 15.

Further, although setting of a display cross section using MPR image data is described above with reference to FIG. 7, a display cross section may be set by using slab MPR image data or slab MIP image data, instead of the MPR image data.

Further, although a case in which a puncture needle is attached to a puncture adapter is described above with reference to FIG. 1, even if a puncture needle is not attached to a puncture adapter, it is possible to operate while seeing an image of the puncture needle without a needle guide.

Moreover, although unequally spaced voxels are interpolated to become isotropic voxels by the interpolation processor 53 shown in FIG. 6, this process may be executed by the two-dimensional image data generator 61 or the three-dimensional image data generator 62 of the image data generator 6.

What is claimed is:

1. An ultrasound imaging apparatus that generates image data based on volume data acquired by three-dimensional scan with ultrasound waves on a target site for examination or treatment using a puncture needle, the ultrasound apparatus comprising: an ultrasound probe configured to scan the target site with ultrasound waves;
a scan controller configured to initially set, based on a first command, for one scan with the ultrasound waves, a first three-dimensional scanning region to include an insertion direction of the puncture needle into the target site and one or more second three-dimensional scanning regions adjacent to the first three-dimensional scanning region and to define the first three-dimensional scanning region according to the insertion direction of the puncture needle, and after the first three-dimensional scanning region and second three-dimensional scanning regions are set, to control, based on a second command, three-dimensional scans on the first three-dimensional scanning region and the second three-dimensional scanning regions;
a volume data microprocessor configured to generate volume data based on received signals acquired from the first three-dimensional scanning region and the second three-dimensional scanning regions by the three-dimensional scan;
an image data microprocessor configured to generate image data by processing the volume data; and
a display configured to display the image data,
wherein the scan controller executes control for three-dimensionally scanning the first three-dimensional scanning region at a higher scanning frequency or a higher scanning-line density than the second three-dimensional scanning regions.

2. The ultrasound imaging apparatus according to claim 1, wherein:
the scan controller is further configured to set a puncture needle scanning region of a predetermined slice thickness with reference to a puncture cross section including the insertion direction of the puncture needle as the first three-dimensional scanning region, and sets treatment target scanning regions of predetermined slice thicknesses adjacent to the puncture needle scanning region in a normal direction of the puncture cross section as the second three-dimensional scanning regions.

3. The ultrasound imaging apparatus according to claim 1, wherein:
the image data microprocessor is further configured to process volume data acquired from the first three-dimensional scanning region or volume data acquired from the first three-dimensional scanning region and the second three-dimensional scanning regions, thereby generating at least one of MPR (Multi-Planar-Reconstruction) image data, slab MPR image data, slab MIP (Maximum Intensity Projection) image data and three-dimensional image data.

4. The ultrasound imaging apparatus according to claim 3, wherein:
the image data microprocessor is further configured to generate the slab MPR image data by calculating an average voxel value of the volume data acquired from the first three-dimensional scanning region in a normal direction of a puncture cross section including the insertion direction of the puncture needle.

5. The ultrasound imaging apparatus according to claim 3, wherein:
the image data microprocessor is further configured to generate the slab MIP image data by extracting a maximum voxel value of the volume data acquired from the first three-dimensional scanning region in a normal direction of a puncture cross section including the insertion direction of the puncture needle.

6. The ultrasound imaging apparatus according to claim 3, wherein:
the image data microprocessor is further configured to synthesize volume data acquired from the first three-dimensional scanning region and volume data acquired from the second three-dimensional scanning regions, and generates the three-dimensional image data by rendering the synthesized volume data.

7. The ultrasound imaging apparatus according to claim 3, wherein:
the image data microprocessor is further configured to synthesize volume data acquired from the first three-dimensional scanning region and volume data acquired from the second three-dimensional scanning regions, and generates the MPR image data by extracting a voxel value in a predetermined cross section of the synthesized volume data.

8. The ultrasound imaging apparatus according to claim 7, further comprising:
a display cross section setting interactive interface configured to allow a user to set a display cross section for the volume data synthesized by using the slab MPR image data or the slab MIP image data,
wherein the image data microprocessor generates the MPR image data by extracting a voxel value in the display cross section of the synthesized volume data.

9. The ultrasound imaging apparatus according to claim 8, wherein:
the display cross section setting interactive interface is further configured to allow a user to set one or more MPR cross sections orthogonal to a slab cross section including the insertion direction of the puncture needle.

10. The ultrasound imaging apparatus according to claim 1, wherein:
the scan controller is further configured to execute control for three-dimensional scanning by executing control for scanning the first three-dimensional scanning region and the second three-dimensional scanning region at a first timing (t10-t11), and
by executing control for scanning only the first three-dimensional scanning region at a second timing (t11-t12) consecutively following the first timing.

11. The ultrasound imaging apparatus according to claim 1, wherein:
the scan controller is further configured to execute control for three-dimensional scanning by executing:
control for scanning the second three-dimensional scanning region once,
control for subsequently scanning the first three-dimensional scanning region for a plurality of times, and
control for subsequently scanning the first three-dimensional scanning region and the second three-dimensional scanning region.

12. The ultrasound imaging apparatus according to claim 1, wherein:
the first three-dimensional scanning region comprises at least two regions and the scan controller is further configured to execute control for three-dimensional scanning by repeatedly executing in order:
control for scanning one of the second three-dimensional scanning regions,
control for scanning the first three-dimensional scanning region,
control for scanning the other of the second three-dimensional scanning regions, and
control for scanning the first three-dimensional scanning region.

13. The ultrasound imaging apparatus according to claim 1, further comprising a plurality of oscillators configured to transmit and receive the ultrasound waves to the object site, wherein the density of oscillators at the position corresponding to the first three-dimensional scanning region is higher than the density of oscillators at the position corresponding to the second three-dimensional scanning region.

14. A method for generating an ultrasound image in which image data is generated based on volume data acquired by three-dimensional scan with ultrasound waves on a target site for examination or treatment using a puncture needle, the method comprising: scanning, by an ultrasound probe, the target site with ultrasound waves;
initially setting, based on a first command, for one scan with the ultrasound waves, a first three-dimensional scanning region including an insertion direction of the puncture needle into the target site and one or more second three-dimensional scanning regions adjacent to the first three-dimensional scanning region and to define the first three-dimensional scanning region according to the insertion direction of the puncture needle, controlling, after the first three-dimensional scanning region and second three-dimensional scanning regions are set, based on a second command, three-dimensional scan on the first three-dimensional scanning region and the second three-dimensional scanning regions, and executing control for three-dimensionally scanning the first three-dimensional scanning region at a higher scanning frequency or a higher scanning-line density than the second three-dimensional scanning regions;
generating volume data based on received signals acquired from the first three-dimensional scanning region and the second three-dimensional scanning regions by the three-dimensional scan;
generating image data by processing the volume data; and displaying the image data.

15. The method for generating an ultrasound image according to claim 14, further comprising:
three-dimensionally scanning the first three-dimensional scanning region at a higher volume rate than the second three-dimensional scanning regions, and scanning the first three-dimensional scanning region at a higher scanning-line density than the second three-dimensional scanning regions is also executed.

16. The method for generating an ultrasound image according to claim 14, wherein:
a puncture needle scanning region of a predetermined slice thickness with reference to a puncture cross section including the insertion direction of the puncture needle is set as the first three-dimensional scanning region, and treatment target scanning regions of predetermined slice thicknesses adjacent to the puncture needle scanning region in a normal direction to the puncture cross section are set as the second three-dimensional scanning regions.

17. The method for generating an ultrasound image according to claim 14, wherein:
at least one of MPR (Multi-Planar-Reconstruction) image data, slab MPR (Maximum Intensity Projection) image data, slab MIP image data and three-dimensional image data is generated by processing volume data acquired from the first three-dimensional scanning region or volume data acquired from the first three-dimensional scanning region and the second three-dimensional scanning regions.

18. The method for generating an ultrasound image according to claim 17, wherein:
the slab MPR image data is generated by calculating an average voxel value of the volume data acquired from the first three-dimensional scanning region, in a normal direction of a puncture cross section including the insertion direction of the puncture needle.

19. The method for generating an ultrasound image according to claim 17, wherein:
the slab MIP image data is generated by extracting a maximum voxel value of volume data acquired from the first three-dimensional scanning region in a normal direction of a puncture cross section including the insertion direction of the puncture needle.

20. The method for generating an ultrasound image according to claim 17, wherein:
volume data acquired from the first three-dimensional scanning region and volume data acquired from the second three-dimensional scanning regions are synthesized, and the three-dimensional image data is generated by rendering the synthesized volume data.

21. The method for generating an ultrasound image according to claim 17, wherein:
volume data acquired from the first three-dimensional scanning region and volume data acquired from the second three-dimensional scanning regions are synthesized, and the MPR image data is generated by extracting a voxel value in a predetermined cross section of the synthesized volume data.

* * * * *